US011523768B2

(12) United States Patent
Sarma et al.

(10) Patent No.: US 11,523,768 B2
(45) Date of Patent: Dec. 13, 2022

(54) IDENTIFYING THE EPILEPTOGENIC ZONE FROM NONSEIZURE RECORDINGS USING NETWORK FRAGILITY THEORY

(71) Applicants: The Johns Hopkins University, Baltimore, MD (US); The Cleveland Clinic Foundation, Cleveland, OH (US)

(72) Inventors: Sridevi Sarma, McLean, VA (US); Adam Li, Thousand Oaks, CA (US); Jorge Gonzalez-Martinez, Moreland Hills, OH (US)

(73) Assignees: The Johns Hopkins University, Baltimore, MD (US); The Cleveland Clinic Foundation, Cleveland, OH (US)

( * ) Notice: Subject to any disclaimer, the term of this patent is extended or adjusted under 35 U.S.C. 154(b) by 281 days.

(21) Appl. No.: 16/348,766

(22) PCT Filed: Nov. 10, 2017

(86) PCT No.: PCT/US2017/061122
§ 371 (c)(1),
(2) Date: May 9, 2019

(87) PCT Pub. No.: WO2018/089806
PCT Pub. Date: May 17, 2018

(65) Prior Publication Data
US 2019/0290185 A1    Sep. 26, 2019

Related U.S. Application Data

(60) Provisional application No. 62/421,037, filed on Nov. 11, 2016.

(51) Int. Cl.
*A61B 5/00* (2006.01)
*A61B 5/372* (2021.01)
(Continued)

(52) U.S. Cl.
CPC ............ *A61B 5/4094* (2013.01); *A61B 5/00* (2013.01); *A61B 5/369* (2021.01); *A61B 5/316* (2021.01); *A61B 5/7253* (2013.01)

(58) Field of Classification Search
None
See application file for complete search history.

(56) References Cited

U.S. PATENT DOCUMENTS 4,417,592 A    11/1983 John
2005/0049649 A1    3/2005 Luders et al.
(Continued)

OTHER PUBLICATIONS

International Search Report from corresponding International Application No. PCT/US2017/061122, dated Jan. 25, 2018.
(Continued)

*Primary Examiner* — Etsub D Berhanu
(74) *Attorney, Agent, or Firm* — Venable LLP; Henry J. Daley; Aziz H. Poonawalla

(57) ABSTRACT

A method of identifying an epileptogenic zone of a subjects brain includes: receiving a plurality N of physiological brain signals that extend over a duration, each of the plurality N of physiological brain signals acquired from the subjects brain; calculating within a time window a state transition matrix based on at least a portion of each of the plurality N of physiological brain signals, wherein the state transition matrix is a linear time invariant model of a network of N nodes corresponding to the plurality N of physiological brain signals; calculating a minimum norm of a perturbation on the state transition matrix that causes the network to transition from a stable state to an unstable state; and assigning a fragility metric to each of the plurality N of physiological brain signals based on the minimum norm of the perturbation for that physiological brain signal.

21 Claims, 8 Drawing Sheets

(51) Int. Cl.
A61B 5/369 (2021.01)
A61B 5/316 (2021.01)

(56) References Cited

U.S. PATENT DOCUMENTS

| | | | | |
|---|---|---|---|---|
| 2011/0130797 | A1* | 6/2011 | Talathi | A61B 5/369 607/3 |
| 2013/0274625 | A1* | 10/2013 | Sarma | A61B 5/4094 600/544 |
| 2014/0094710 | A1 | 4/2014 | Sarma et al. | |
| 2014/0121554 | A1* | 5/2014 | Sarma | A61B 5/4094 600/544 |
| 2014/0128762 | A1 | 5/2014 | Han et al. | |
| 2015/0366482 | A1* | 12/2015 | Lee | A61B 5/055 600/411 |
| 2016/0287118 | A1* | 10/2016 | Sarma | A61B 5/291 |

OTHER PUBLICATIONS

Written Opinion from corresponding International Application No. PCT/US2017/061122, dated Jan. 25, 2018.
Adelson et al., "Chronic invasive monitoring for identifying seizure foci in children", Neurosurgery clinics of North America. 1995;6(3):491-504.
Anderson et al., "Implantation of a responsive neurostimulator device in patients with refractory epilepsy", Neurosurg Focus. (2008) 25:E12.
Bancaud et al., "[Neurophysiopathological hypothesis on startle epilepsy in man]", Revue neurologique. 1975;131(8):559-571.
Bancaud et al., "Activation by Megimide in the topographic diagnosis of focal cortical epilepsies (clinical EEG and SEEG study)", Electroencephalography and clinical neurophysiology. 1969;26(6):640.
Bartolomei et al., "Neural networks involving the medial temporal structures in temporal lobe epilepsy", Clinical neurophysiology : official journal of the International Federation of Clinical Neurophysiology. 2001;112(9):1746-1760.
Begley et al., "The cost of epilepsy in the United States: an estimate from population-based clinical and survey data", Epilepsia (2000) 41: 342-351.
Begley et al., "The direct cost of epilepsy in the United States: A systematic review of estimates", Epilepsia. 2015;56(9):1376-1387.
Berg "Identification of Pharmacoresistant Epilepsy", Neurol Clin 27 (2009) 1003-1013.
Berg et al., "Defining intractability: comparisons among published definitions," Epilepsia. 2006;47(2):431-436.
Bonini et al., "Epileptogenic networks in seizures arising from motor systems", Epilepsy research. 2013;106(1-2):92-102.
Brodie et al., "Commission on European Affairs: appropriate standards of epilepsy care across Europe", ILEA. Epilepsia. 1997;38(11):1245-1250.
Bulacio et al., "Long-term seizure outcome after resective surgery in patients evaluated with intracranial electrodes", Epilepsia. 2012;53(10):1722-1730.
Burns et al., "Network dynamics of the brain and influence of the epileptic seizure onset zone", Proceedings of the National Academy of Sciences, vol. 111, No. 49, Nov. 17, 2014, pp. E5321-E5330, XP055358609.
Cardinale et al., "Stereo-electroencephalography safety and effectiveness: Some more reasons in favor of epilepsy surgery", Epilepsia. 2013;54(8):1505-1506.
Curry et al. "MR-guided stereotactic laser ablation of epileptogenic foci in children", Epilepsy & behavior: E&B. 2012;24(4):408-414.
Ehrens et al., "Closed-loop control of a fragile network: application to seizure-like dynamics of an epilepsy model", Frontiers in Neuroscience, vol. 9, Mar. 3, 2015, XP055693678.
Engel et al., "Presurgical evaluation for partial epilepsy: relative contributions of chronic depth-electrode recordings versus FDG-PET and scalp-sphenoidal ictal EEG", Neurology. 1990;40(11):1670-1677.

Fisher "Therapeutic devices for epilepsy", Annals of neurology. 2012;71(2):157-168.
Fountas et al., "Implantation of a closed loop stimulation in the management of medically refractory focal epilepsy: a technical note", Stereotact Funct Neurosurg.(2005) 83:153-58.
Gonzalez-Martinez et al., "Stereoelectroencephalography in children with cortical dysplasia: technique and results. Child's nervous system", ChNS : official journal of the International Society for Pediatric Neurosurgery. 2014;30(11):1853-1857.
Gonzalez-Martinez et al., "Stereoelectroencephalography in the "difficult to localize" refractory focal epilepsy: early experience from a North American epilepsy center", Epilepsia. 2013;54(2):323-330.
Gumnit et al., "Guidelines for Essential Services, Personnel, and Facilities in Specialized Epilepsy Centers", (2010) 2010 NAEC Guidelines for Specialized Epilepsy Centers. Retrieved from http://naec-epilepsy.orxispec care/documents/NAEC-FinalGuidelineswithrruralcenterrevision.pdf.
Hawasli et al., "Laser ablation as treatment strategy for medically refractory dominant insular epilepsy: therapeutic and functional considerations", Stereotactic and functional neurosurgery. 2014;92(6):397-404.
Hermann et al., "Cognitive prognosis in chronic temporal lobe epilepsy", Annals of neurology. 2006;60(1):80-87.
Jirsa et al., "On the nature of seizure dynamics. Brain : a journal of neurology", 2014;137(Pt 8):2210-2230.
Jiruska et al., "Effects of direct brain stimulation depend on seizure dynamics", (2010) Epilepsia 51: S93-S97.
Jobst et al., "Brain stimulation for the treatment of epilepsy", Epilepsia (2010) 51: S88-S92.
Kwan et al., "Drug-resistant epilepsy", N Engl J Med. 2011; 365(10): 919.
Kwan et al., "Early identification of refractory epilepsy", N Engl J Med. Feb. 3, 2000;342(5): 314-9.
Lewis et al., "MR-guided laser interstitial thermal therapy for pediatric drug-resistant lesional epilepsy", Epilepsia. 2015.
Lüders et al., "The epileptogenic zone: general principles. Epileptic Disord", Aug. 2006;8 Suppl 2:S1-9. Erratum in: Epileptic Disord. Jun. 2008;10(2):191.
McIntosh et al., "Temporal lobectomy: long-term seizure outcome, late recurrence and risks for seizure recurrence", Brain. Sep. 2004;127(Pt 9):2018-30. Epub Jun. 23, 2004.
Morell et al., "Long term safety and efficacy of the RNSTM system in adults with medically intractable partial onset seizures", (2008) Proc. American Epilepsy Society Annual Meeting. Abstract No. 8536. www.aesnet.org.
Morrell "On behalf of the RNS System in Epilepsy Study Group. Responsive Cortical stimulation for the treatment of medically intractable partial epilepsy". Neurology (2011) vol. 77, pp. 1295-1304.
Morrell M. (2006) Brain stimulation for epilepsy: Can scheduled or responsive neurostimulation stop seizures? Curr Opinion Neural. 19:164-168.
Najm et al., "Definition of the epileptogenic zone in a patient with non-lesional temporal lobe epilepsy arising from the dominant hemisphere", Epileptic disorders : international epilepsy journal with videotape. 2006;8 Suppl 2:S27-35.
Ngugi et al., "Estimation of the burden of active and life-time epilepsy: a meta-analytic approach", Epilepsia. (2010) vol. 51, No. 5, pp. 883-890.
Sritharan et al., "Fragility in Dynamic Networks: Application to Neural Networks in the Epileptic Cortex", Neural Computation, Oct. 1, 2014, vol. 26, No. 10, pp. 2294-2327.
Sritharan et al., "Fragility in Networks: Application to the Epileptic Brain", IFAC The 2012 IFAC Workshop on Automatic Control in Offshore Oil and Gas Production, Jan. 1, 2014, vol. 47, No. 3, pp. 7505-7510.
Sun et al., "Responsive Cortical Stim-ulation for the Treatment of Epilepsy", Neurotherapeutics. Jan. 2008;5:68-74.
Widdess-Walsh et al., "Subdural electrode analysis in focal cortical dysplasia: predictors of surgical outcome", Neurology. 2007;69(7):660-667.

(56) References Cited

OTHER PUBLICATIONS

Willie et al., "Real-time magnetic resonance-guided stereotactic laser amygdalohippocampotomy for mesial temporal lobe epilepsy", Neurosurgery. (2014) vol. 74, No. 6, pp. 569-584; discussion 584-565.
Esquenazi et al., "Stereotactic laser ablation of epileptogenic periventricular nodular heterotopia", Epilepsy Research, (2014), vol. 108, No. 3, pp. 547-554.
Ferro et al., "Stability of latent classes in group-based trajectory modeling of depressive symptoms in mothers of children with epilepsy: an internal validation study using a bootstrapping procedure", Social psychiatry and psychiatric epidemiology, (2013), vol. 48, No. 7, pp. 1077-1086.
Gonzalez-Martinez et al., "Stereoelectroencephalography in children and adolescents with difficult-to-localize refractory focal epilepsy", Neurosurgery, (2014), vol. 75, No. 3, pp. 258-268; discussion 267-258.
Gonzalez-Martinez et al., "Stereotactic placement of depth electrodes in medically intractable epilepsy", Journal of Neurosurgery, (2014), vol. 120, No. 3, pp. 639-644.
Gonzalez-Martinez et al., "Indications and selection criteria for invasive monitoring in children with cortical dysplasia", Child's Nervous System, (2014), vol. 30, No. 11, pp. 1823-1829.
Gonzalez-Martinez et al., "Robot-assisted stereotactic laser ablation in medically intractable epilepsy: operative technique", Neurosurgery, (2014), vol. 10, Suppl 2, pp. 167-172; discussion 172-163.
Gonzalez-Martinez, "Convergence of Stereotactic Surgery and Epilepsy: The Stereoelectroencephalography Method", Neurosurgery, (2015), vol. 62, Suppl 1, pp. 117-122.
Gonzalez-Martinez et al., "Long-term seizure outcome in reoperation after failure of epilepsy surgery", Neurosurgery, (2007), vol. 60, No. 5, pp. 873-880; discussion 873-880.
Gross et al., "Less is more: novel less-invasive surgical techniques for mesial temporal lobe epilepsy that minimize cognitive impairment", Current Opinion in Neurology, (2015), vol. 28, No. 2, pp. 182-191.
Hamer et al., "Complications of invasive video-EEG monitoring with subdural grid electrodes", Neurology, (2002), vol. 58, No. 1, pp. 97-103.
Jayakar et al., "Subdural monitoring in the evaluation of children for epilepsy surgery", Journal of Child Neurology, (1994), vol. 9, Suppl 2, pp. 61-66.
Jayakar, "Invasive EEG monitoring in children: when, where, and what?", Journal of Clinical Neurophysiology : Official Publication of the American Electroencephalographic Society, (1999), vol. 16, No. 5, pp. 408-418.
Jeha et al., "Predictors of outcome after temporal lobectomy for the treatment of intractable epilepsy", Neurology, (Jun. 27, 2006), vol. 66, No. 12, pp. 1938-1940.
Kwan et al., "Definition of refractory epilepsy: defining the indefinable? ", The Lancet. Neurology, (2010), vol. 9, No. 1, pp. 27-29.
Lee et al., "Complications and results of subdural grid electrode implantation in epilepsy surgery", Surgical Neurology, (2000), vol. 54, No. 5, pp. 346-351.
Lega et al., "Cortico-cortical evoked potentials for sites of early versus late seizure spread in stereoelectroencephalography", Epilepsy Research, (2015), vol. 115, pp. 17-29.
Lopez-Gonzalez et al., "Epilepsy surgery of the temporal lobe in pediatric population: a retrospective analysis", Neurosurgery, (2012), vol. 70, No. 3, pp. 684-692.
Luders et al., "Epilepsy surgery in patients with malformations of cortical development", Current Opinion in Neurology, (2006), vol. 19, No. 2, pp. 169-174.
Medvid et al., "Current Applications of MRI-Guided Laser Interstitial Thermal Therapy in the Treatment of Brain Neoplasms and Epilepsy: A Radiologic and Neurosurgical Overview", AJNR. American Journal of Neuroradioiogy, Medvid, (Nov. 2015), pp. 1998-2006.
Mullin et al., "Is Stereotacticelectroencephalography Safe? A Systematic Review and Meta-Analysis of Stereo-electroencephalography-Related Complications", Neurosurgery, (Aug. 2016), vol. 63, No. 1, p. 211.
Munari et al., "Stereotactic investigations in frontal lobe epilepsies", Acta neurochirurgica. Supplementum, (1989) vol. 46, pp. 9-12.
Murray et al., "Cost of refractory epilepsy in adults in the USA", Epilepsy Research, (1996), vol. 23, No. 2, pp. 139-148.
Nair et al., "Chronic subdural electrodes in the management of epilepsy", Clinical Neurophysiology : Official Journal of the International Federation of Clinical Neurophysiology, (2008), vol. 119, No. 1, pp. 11-28.
Najm et al., "The use of subdural grids in the management of focal malformations due to abnormal cortical development", Neurosurgery Clinics of North America, (2002), vol. 13, No. 1, pp. 87-92, viii-ix.
Rosenow et al., "Presurgical evaluation of epilepsy", Brain : A Journal of Neurology, (2001), vol. 124, Pt 9, pp. 1683-1700.
Rydenhag et al., "Complications of Epilepsy Surgery after 654 Procedures in Sweden, Sep. 1990-1995: A Multicenter Study Based on the Swedish National Epilepsy Surgery Register", Neurosurgery, (2001), vol. 49, No. 1, pp. 51-56; discussion 56-57.
See et al., "Surgical Outcomes in Patients With Extratemporal Epilepsy and Subtle or Normal Magnetic Resonance Imaging Findings", Neurosurgery, (Jul. 2013), vol. 73, No. 1, pp. 68-77; discussion 76-7.
Serletis et al., "The stereotactic approach for mapping epileptic networks: a prospective study of 200 patients", Journal of Neurosurgery, (2014), vol. 121, No. 5, pp. 1239-1246.
Spiegler et al., "Systematic approximations of neural fields through networks of neural masses in the virtual brain", NeuroImage, (2013), vol. 83, pp. 704-725.
Sun et al., "Tissue Ablation Dynamics During Magnetic Resonance-Guided, Laser-Induced Thermal Therapy", Neurosurgery, (2015), vol. 77, No. 1, pp. 51-58; discussion 58.
Talairach et al., "Application of stereotactic concepts to the surgery of epilepsy", Acta Neurochirurgica. Supplementum, (1980), vol. 30, pp. 35-54.
Talairach et al., "Stereotaxic exploration in frontal epilepsy", Advances in Neurology, (1992), vol. 57, pp. 651-688.
Thornton et al., "Epileptic Networks in Focal Cortical Dysplasia Revealed Using Electroencephalography—Functional Magnetic Resonance Imaging", Annals of Neurology, (2011), vol. 70, No. 5, pp. 822-837.
Tovar-Spinoza et al.,"The Use of MRI-Guided Laser-Induced Thermal Ablation for Epilepsy", Child's Nervous System : ChNS : Official Journal of the International Society for Pediatric Neurosurgery, (2013), vol. 29, No. 11, pp. 2089-2094.
Vadera et al., "Stereoelectroencephalography Following Subdural Grid Placement for Difficult to Localize Epilepsy", Neurosurgery, (2013), vol. 72, No. 5, pp. 723-729; discussion 729.
Vaugier et al., "Neural Networks Underlying Hyperkinetic Seizures of "temporal lobe" Origin", Epilepsy Research, . (2009), vol. 86, Nos. 2-3, pp. 200-208.
Waseem et ai., "Laser Ablation Therapy: An alternative Treatment for Medically Resistant Mesial Temporal Lobe Epilepsy After Age 50", Epilepsy & Behavior: E&B, (2015), vol. 51, pp. 152-157.
Wendling et al., "Interpretation of interdependencies in Epileptic Signals Using a Macroscopic Physiological Model of the EEG", Clinical Neurophysiology: Official Journal of the International Federation of Clinical Neurophysiology, (2001), Vo. 112, No. 7, pp. 1201-1218.
Willie et al., "Role of Repeat Ablation to Treat Seizure Recurrence Following Stereotactic Laser Amygdalohippocampotomy", Neurosurgery, (2015), vol. 62, Suppl 1, pp. 233-234.
Wyllie et al., "Subdural Electrodes in the Evaluation for Epilepsy Surgery in Children and Adults", Neuropediatrics, (1988), vol. 19, No. 2, pp. 80-86.
NeuroPace. RNS System Clinical Summary. (2013) Retrieved from http://www.neuropace.com/productJpdfs/RNS-300M Clinical Summary EN.pdf.

(56) References Cited

OTHER PUBLICATIONS

Bancaud et al., "Generalized epileptic seizures elicited by electrical stimulation of the frontal lobe in man", Electroencephalography and clinical neurophysiology, (1974), vol. 37, pp. 275-282.

Bancaud et al., "Behavioral manifestations induced by electric stimulation of the anterior cingulate gyrus in man]", Revue Neurologique, (Oct. 1976), vol. 132, No. 10, pp. 705-744. Abstract Only.

Bancaud et al., "d'Ammon's horn and amygdaline nucleus: clinical and electric effects of their stimulation in man", Revue Neurologique, (1966), vol. 115, No. 3, pp. 329-352. (Partial English translation of original French article).

Munari et al., "Role of the amygdala in the occurence of oro-alimentary signs of during epileptic seizures in man (author's transl)", Revue d'electroencephalographie et de neurophysioiogie clinique, (1979), vol. 9, No. 3, pp. 236-240. (Partial English translation of original French article).

Munari et al., "Cerebral concentrations of anticonvulsants in patients with epilepsy of tumoral origin (author's transl)", Revue d'electroencephalographie et de neurophysioiogie clinique, (1982), vol. 12, No. 1, pp. 38-43. (Partial English translation of original French article).

Talairach et al., "Amygdalo-hippocampal partial destruction by yttrium-90 in the treatment of certain epilepsies of rhinencephalic manifestation", Neuro-Chirurgie, (1965), vol. 11, No. 3, pp. 233-240. (Full English translation of original French article).

Bancaud et al., "Activation by Megimide in the topographic diagnosis of focal cortical epilepsies", (Clinical study, EEG and SEEG)]. French Language Electroencephalography Society, Revue Neurologique, (1968), vol. 119, No. 3, pp. 320-325. (Translation of article introduction from original French).

\* cited by examiner

ACTUAL EEG DATA.

SIMULATED EEG DATA.

IDENTIFYING THE EPILEPTOGENIC ZONE FROM NONSEIZURE RECORDINGS USING NETWORK FRAGILITY THEORY

This application is a National Stage Application under 35 U.S.C. 371 of International Application No. PCT/US2017/06122, filed Nov. 10, 2017, which claims priority to U.S. Provisional Application No. 62/421,037 filed Nov. 11, 2016, the entire contents of which are hereby incorporated by reference.

This invention was made with government support under T32 EB003383 awarded by the National Institutes of Health. The government has certain rights in the invention.

BACKGROUND

1. Field of Invention

The field of the currently claimed embodiments of this invention relates to methods and systems for identifying epileptic zones of a subject's brain.

2. Discussion of Related Art

Over 20 million people in the world suffer from medically refractory epilepsy (MRE). MRE patients are frequently hospitalized and burdened by epilepsy-related disabilities, such as delay in neurocognitive development and incapacity in obtaining driving privileges—making this population a substantial contributor to the $16 billion dollars spent annually in the US treating epilepsy. Approximately 50% of MRE patients have focal MRE, where a hypothetical region in the brain, the epileptogenic zone (EZ), is the source of the seizures.

Epilepsy is a brain disorder, characterized by chronically recurrent seizures resulting from excessive electrical discharges from groups of neurons [1]. Epilepsy affects over 50 million people worldwide and over 30% of all individuals with epilepsy have intractable seizures, which cannot completely be controlled by medical therapy [2,3]. That is, seizures continue to occur despite treatment with a maximally tolerated dose of at least two anti-epilepsy drugs (AEDs). The direct cost of assessing and treating patients with MRE ranges from $3-4 billion annually ($16 billion in direct and indirect costs) in the US (based on a 1996 and 2015 publications) [4-6]. 80% of these costs are accounted by patients whose seizures are not adequately controlled by AEDs [5]. The burden of MRE, however, is much greater than financial costs. MRE is a debilitating illness where individuals lose their independence, causing profound behavioral, psychological, cognitive, social, financial and legal issues [7-9]. Recurrent seizures impair socialization and psychological development during formative years and may lead to an inability to obtain an education, gainful employment, or driving privileges.

The current methods for diagnosing and treating MRE are limited by high morbidity and low efficacy related to invasive monitoring in MRE. Despite the heavy sequelae from MRE, there is a potentially curative procedure—surgical resection of the epileptogenic zone (EZ), which can be defined as the minimal area of brain tissue responsible for generating the recurrent seizure activity [10,11]. However, to be effective, this procedure depends on correct identification of the EZ, which is often unclear [12]. A comprehensive pre-surgical evaluation is necessary to pinpoint the EZ as well as to identify the risks of neurologic morbidity such as visual or speech impairment [13-16]. Various non-invasive and invasive methods are used. Non-invasive techniques include scalp EEG and video-EEG monitoring, neuropsychological tests, speech-language studies, and brain imaging (MRI, PET, Ictal SPECT). Of these methods, the highest predictor of surgical success is identification of a single visible MRI lesion [12,17,18]. In patients with non-lesional MRI, localization and surgical success in seizure control are even more challenging [17].

Despite the advances in imaging technologies, a significant number of surgical patients with focal epilepsy (~25%) continue to have non-lesional MRIs [17,19]. When the non-invasive methods of localization fail to identify the epileptogenic zone (EZ), the method of last resort is an invasive evaluation, comprising the implantation of subdural grid electrodes (SDE) through open craniotomies, and subsequent prolonged extra-operative monitoring in a dedicated Epilepsy Monitoring Unit (EMU) [19,20]. Subdural grids and strips are the most common invasive method used in the United States [12,21]. Despite the high spatial resolution provided by the subdural methodology, deep epileptic foci and, consequently, the 3D organization of a given EZ cannot be sampled with adequate spatial and temporal resolution [22,23]. In addition, subdural grids require relatively large craniotomies and are, in general, limited to exploration of one hemisphere, providing only a two dimensional picture of a complex epileptic network [24,25]. In addition, current invasive evaluations with subdural grids are very expensive, and are associated with multiple complications including hemorrhages, infections, and neurological deficits [26].

Treatment for MRE by resection of the EZ is often effective, provided the EZ is reliably identified. Focal epilepsy, however, is fundamentally a network-based disease. The EZ is composed and connected to a large scale neuronal network whose other nodes may also exhibit abnormal neural activity either concurrently or subsequently. In patients without MM detectable lesions, characterization and differentiation of the EZ from these other nodes in the epileptic network can be difficult, even with the use of invasive recordings. Consequently, despite large brain regions being removed, guided by invasive evaluations, sustained surgical success rates barely reach 30%. Such disappointing outcomes associated with high morbidity rates are often due to imprecise and/or inaccurate localization of the EZ in association with attempting to treat a network disease using a single focal resection.

There thus remains a need for improved systems and methods for identifying epileptic zones of a subject's brain.

SUMMARY

According to some embodiments of the invention, a method of identifying an epileptogenic zone of a subject's brain includes: receiving a plurality N of physiological brain signals that extend over a duration, each of the plurality N of physiological brain signals acquired from the subject's brain; calculating within a time window a state transition matrix based on at least a portion of each of the plurality N of physiological brain signals, wherein the state transition matrix is a linear time invariant model of a network of N nodes corresponding to the plurality N of physiological brain signals; calculating, for each of the plurality N of physiological brain signals, a minimum norm of a perturbation on the state transition matrix that causes the network to transition from a stable state to an unstable state; and assigning a fragility metric to each of the plurality N of physiological brain signals based on the minimum norm of the perturbation for that physiological brain signal.

According to some embodiments of the invention, a non-transitory computer-readable medium for identifying an epileptogenic zone of a subject's brain includes computer-executable code, the code when executed by a computer causes the computer to: receive a plurality N of electrical signals that extend over a duration, each of the plurality N of physiological brain signals acquired from the subject's brain; calculate within a time window a state transition matrix based on at least a portion of each of the plurality N of physiological brain signals, wherein the state transition matrix is a linear time invariant model of a network of N nodes corresponding to the plurality N of physiological brain signals; calculate, for each of the plurality N of physiological brain signals, a minimum norm of a perturbation on the state transition matrix that causes the network to transition from a stable state to an unstable state; and assign a fragility metric to each of the plurality N of physiological brain signals based on the minimum norm of the perturbation for that physiological brain signal.

According to some embodiments of the invention, a system for identifying an epileptogenic zone of a subject's brain includes a computer configured to: receive a plurality N of physiological brain signals that extend over a duration, each of the plurality N of physiological brain signals acquired from the subject's brain; calculate within a time window a state transition matrix based on at least a portion of each of the plurality N of physiological brain signals, wherein the state transition matrix is a linear time invariant model of a network of N nodes corresponding to the plurality N of physiological brain signals; calculate, for each of the plurality N of physiological brain signals, a minimum norm of a perturbation on the state transition matrix that causes the network to transition from a stable state to an unstable state; assigning a fragility metric to each of the plurality N of physiological brain signals based on the minimum norm of the perturbation for that physiological brain signal.

DETAILED DESCRIPTION

Figure 1:
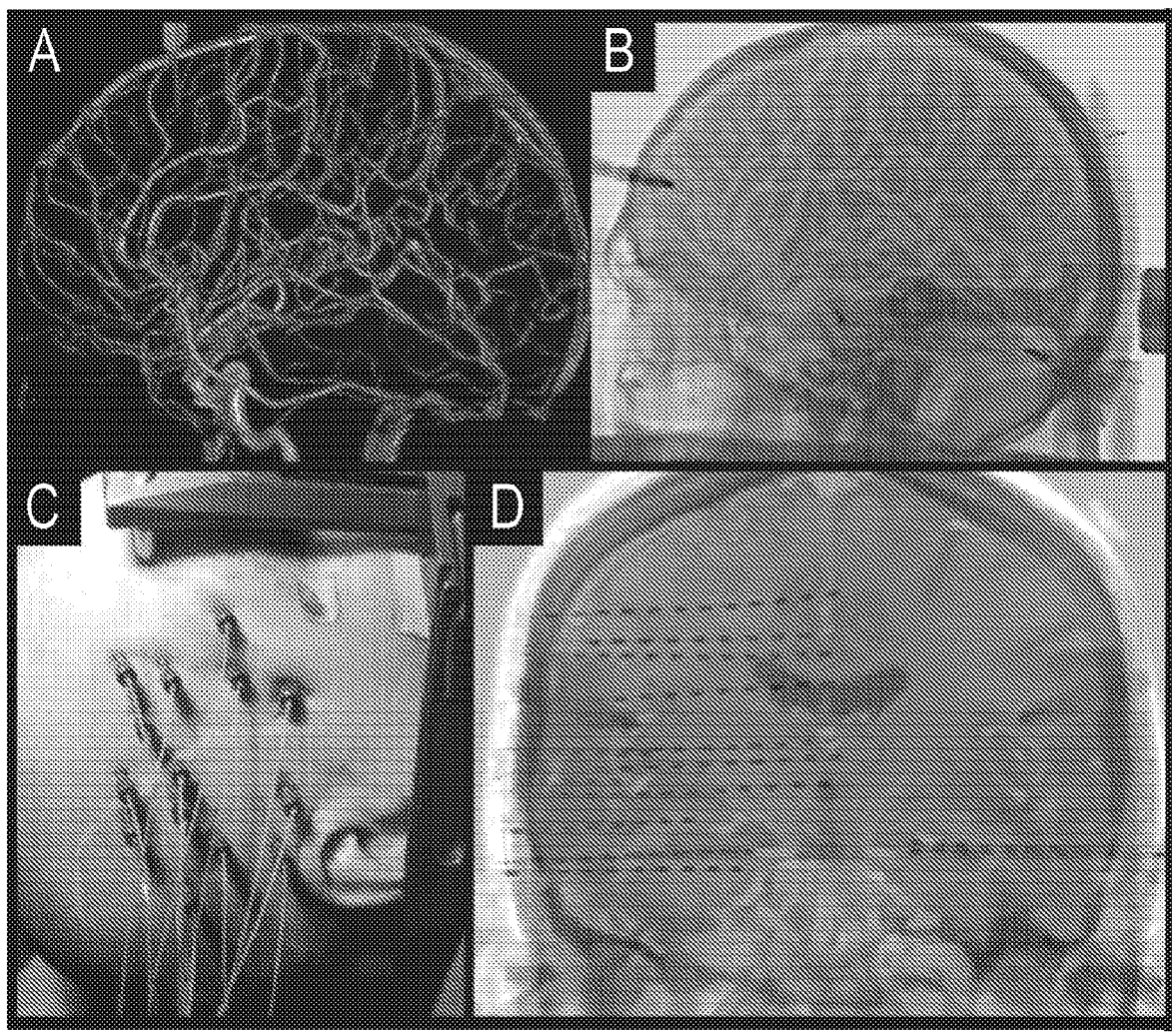
FIG. 1 shows imaging fusion and placement of multiple electrodes using the SEEG method according to some embodiments. Images A and B show pre-op imaging with MRA and CT angiography, respectively. Together, electrode trajectories are safely planned, avoiding vascular structures, and limiting the risk of bleeding and electrode misplacement. Image C is a photograph showing 14 electrodes at the skin surface. Image D is an intraoperative image showing a superposition of bilateral SEEG electrodes on a coronal MRI T1W image. Note the precise parallel placement, with tips terminating at the midline or dural surface.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The methods described herein can be used to create more precise and accurate maps of the EZ within epileptic networks in patients with MRE. These maps will strategically guide multiple laser ablations of network nodes resulting in the complete extinction of the epileptic activity, avoiding large resections and high morbidity rates. EZTrack is a computation tool that can reveal the EZ in patients with MRI-negative focal epilepsy. The EZ maps can be created through the application of a novel algorithm that detects "fragility" of nodes in the epileptic network. Fragility of each node in a network (i.e., each implanted electrode) is defined as the minimum perturbation that can be applied to the electrode's connectivity with its neighbors that destabilizes the entire network. Fragility is derived using dynamical systems theory and computed from electrophysiological data prior to seizure onset. The most fragile network nodes correspond to the EZ. The analysis according to embodiments of the invention is in stark contrast to existing algorithms that either process each EEG channel individually, ignoring network dynamics completely, or attempt to track network dynamics by computing pairwise correlations over time, thus only tracking local dynamics.

According to some embodiments of the invention, a method of identifying an epileptogenic zone of a subject's brain includes: receiving a plurality N of physiological brain signals that extend over a duration, each of the plurality N of physiological brain signals acquired from the subject's brain; calculating within a time window a state transition matrix based on at least a portion of each of the plurality N of physiological brain signals, wherein the state transition matrix is a linear time invariant model of a network of N nodes corresponding to the plurality N of physiological brain signals; calculating, for each of the plurality N of physiological brain signals, a minimum norm of a perturbation on the state transition matrix that causes the network to transition from a stable state to an unstable state; and assigning a fragility metric to each of the plurality N of physiological brain signals based on the minimum norm of the perturbation for that physiological brain signal.

According to some embodiments, calculating the state transition matrix comprises calculating a matrix A such that $$x(t+1)=Ax(t)$$

where x(t) is a state vector that describes activity of the network at time t, wherein activity of the network corresponds to the plurality N of physiological brain signals, and A is the state transition matrix for the time window.

According to some embodiments, calculating the minimum norm of the perturbation comprises calculating a minimum norm of the perturbation for each row or column of the state transition matrix. According to some embodiments, assigning the fragility metric to each of the plurality N of physiological brain signals is based on the minimum norm of the perturbation for the corresponding row or column of the state transition matrix.

According to some embodiments, the method further includes generating a heat map indicating a relative probability for each of the plurality N of physiological brain signals of being in the epileptogenic zone based on the fragility metric assigned to each of the plurality N of physiological brain signals. According to some embodiments, the method further includes displaying an indication of the fragility metric assigned to each of the plurality N of physiological brain signals at a plurality of points in time within the duration. According to some embodiments, each of the plurality N of physiological brain signals corresponds to one of a plurality N of electrodes in the subject's brain.

According to some embodiments of the invention, a non-transitory computer-readable medium for identifying an epileptogenic zone of a subject's brain includes computer-executable code, the code when executed by a computer causes the computer to: receive a plurality N of electrical signals that extend over a duration, each of the plurality N of physiological brain signals acquired from the subject's brain; calculate within a time window a state transition matrix based on at least a portion of each of the plurality N of physiological brain signals, wherein the state transition matrix is a linear time invariant model of a network of N nodes corresponding to the plurality N of physiological brain signals; calculate, for each of the plurality N of physiological brain signals, a minimum norm of a perturbation on the state transition matrix that causes the network to transition from a stable state to an unstable state; and assign a fragility metric to each of the plurality N of physiological brain signals based on the minimum norm of the perturbation for that physiological brain signal.

According to some embodiments, the code when executed by a computer causes the computer to calculate the state transition matrix by calculating a matrix A such that $$x(t+1)=Ax(t)$$

where x(t) is a state vector that describes activity of the network at time t, and A is the state transition matrix for the time window.

According to some embodiments, the code when executed by a computer causes the computer to calculate the minimum norm of the perturbation by calculating a minimum norm of the perturbation for each row or column of the state transition matrix. According to some embodiments, the code when executed by a computer causes the computer to assign the fragility metric to each of the plurality N of physiological brain signals by assigning a fragility metric to each of the plurality N of physiological brain signals based on the minimum norm of the perturbation for the corresponding row or column of the state transition matrix.

According to some embodiments, the code when executed by a computer further causes the computer to generate a heat map indicating a relative probability for each of the plurality N of physiological brain signals of being in the epileptogenic zone based on the fragility metric assigned to each of the plurality N of physiological brain signals. According to some embodiments, the code when executed by a computer further causes the computer to display an indication of the fragility metric assigned to each of the plurality N of physiological brain signals at a plurality of points in time within the duration. According to some embodiments, each of the plurality N of physiological brain signals corresponds to one of a plurality N of electrodes in the subject's brain.

According to some embodiments of the invention, a system for identifying an epileptogenic zone of a subject's brain includes a computer configured to: receive a plurality N of physiological brain signals that extend over a duration, each of the plurality N of physiological brain signals acquired from the subject's brain; calculate within a time window a state transition matrix based on at least a portion of each of the plurality N of physiological brain signals, wherein the state transition matrix is a linear time invariant model of a network of N nodes corresponding to the plurality N of physiological brain signals; calculate, for each of the plurality N of physiological brain signals, a minimum norm of a perturbation on the state transition matrix that causes the network to transition from a stable state to an unstable state; assigning a fragility metric to each of the plurality N of physiological brain signals based on the minimum norm of the perturbation for that physiological brain signal.

According to some embodiments, the computer is further configured to calculate the state transition matrix by calculating a matrix A such that $$x(t+1)=Ax(t)$$

where x(t) is a state vector that describes activity of the network at time t, and A is the state transition matrix for the time window.

According to some embodiments, the computer is further configured to calculate the minimum norm of the perturbation by calculating a minimum norm of the perturbation for each row or column of the state transition matrix. According to some embodiments, the computer is further configured to assign the fragility metric to each of the plurality N of physiological brain signals by assigning a fragility metric to each of the plurality N of surgically implanted electrodes based on the minimum norm of the perturbation for the corresponding row or column of the state transition matrix.

According to some embodiments, the computer is further configured to generate a heat map indicating a relative probability for each of the plurality N of physiological brain signals of being in the epileptogenic zone based on the fragility metric assigned to each of the plurality N of physiological brain signals. According to some embodiments, the computer is further configured to display an indication of the fragility metric assigned to each of the plurality N of physiological brain signals at a plurality of points in time within the duration. According to some embodiments, each of the plurality N of physiological brain signals corresponds to one of a plurality N of electrodes in the subject's brain.

The methods described herein may be executed by a processor. The processor can be a dedicated "hard-wired" device, or it can be a programmable device. For example, it can be, but is not limited to, a computer, a work station, or any other suitable electronic device for the particular application. In some embodiments, it can be integrated into a unit or it can be attachable, remote, and/or distributed. The processor may be in communication with a user interface. The user interface may include an input device such as a keyboard or touch screen. The user interface may also include a display device. The processor may be configured to display information on the display device. For example, the processor may be configured to display an indication of an identified epileptogenic zone on the display device.

Although the recordings from subdural intracranial electrodes should significantly improve the ability to localize and delineate the extent of the EZ, a failure to accomplish this goal is not uncommon [12], especially in patients with non-lesional MRIs [12,30]. The reasons for the sub-optimal results are: (i) the untrue and widespread concept that the organization and spread of seizures are caused by well-defined and focal superficial cortical areas (the epileptic focus), and (ii) the incorrect identification of the EZ within the epileptic network electrophysiological signatures from intracranial EEG recordings that would allow a more precise and restrict EZ localization [23,38,39]. Instead, the systems and methods described herein are based on the concept that the epileptic activity is generated, organized and spread through a more widespread and complex epileptic network, composed of different nodes and pathways, with different roles and weights [31-37]; and new data analysis tools should be used to assist clinicians in localizing the EZ.

Today, the process of identifying the EZ involves visually inspecting tens to hundreds of EEG signals without the assistance of sophisticated network connectivity analyses. Currently, epileptologists study the onset of seizure events that occur over several days. Seizure events are typically marked by the early presence of beta-band activity ('beta buzz") or bursts of high frequency oscillations (100-300 Hz), which typically occur milliseconds before the clinical onset of seizures. Assuming the epileptic cortex generates epileptiform activity, which then entrains other regions into a clinical seizure [40], channels where these onset features first appear are commonly identified as the EZ. Electrodecremental responses (loss of rhythmic activity) are also often observed. In general, epileptologists look at a variety of signatures to make their decision [40]. Despite all of these possible EEG signatures, the definition of the EZ may remain unclear for non-lesional patients.

The most rapid initial seizure recurrence rate is for non-lesional patients with normal MRI (70% of all recurrences occur within the first month after surgery), while patients with abnormal MRIs have a 30% chance of seizure recurrence within one month post surgery [12]. The failures for patients with non-lesional MRIs are likely caused by non-identification of the fundamental features of epileptic networks responsible for the seizures origin and primary organization of the epileptic activity and, consequently, the non-resection or non-adequate modulation of the important nodes and pathways that fundamentally characterized the network. As such, any intervention aimed at improving the pre-operative anatomo-functional definition of the EZ, and thus slowing down the initial steep recurrence phase observed after surgery (especially in patients who have normal MRIs), would greatly improve patient outcomes. In summary, the systems and methods according to some embodiments of the invention are highly significant because: 1) A significant number of epilepsy patients do not respond to drugs, leaving them severely impaired.

2) All treatments often involve highly invasive and lengthy pre-surgical evaluation, causing increased morbidity, hospital resources, and patient costs.

3) The current clinical paradigm of seizure localization prevents the precise characterization of EZ and does not exploit sophisticated data analytics, despite being in an era of big data technology.

The systems and methods according to some embodiments of the invention can increase the success rate of surgical treatment for patients with MRE by promoting more precise localization of the EZ guided by sophisticated data analytics.

The systems and methods according to some embodiments of the invention can minimize pre-surgical evaluation invasiveness and time, resulting in reduced treatment costs, resources, and patient risks.

The dynamical systems theory concepts developed here to localize the EZ can be applied to mechanistic models to identify mechanisms of critical transitions such as seizure onset and termination in epileptic networks; and can further development of new therapies.

The systems and methods according to some embodiments of the invention can lay the necessary foundation for revolutionizing treatment for MRE, addressing the significant challenges mentioned above. The treatment approach may entail (i) a minimally invasive extra-operative intracranial EEG monitoring method that is emerging as the standard practice in more and more US centers, (ii) the network concept of the EZ and our novel computational tool, EZTrack, that accurately identifies the EZ from SEEG data and that will guide (iii) a minimally invasive laser ablation treatment.

The embodiments of the invention can be applied to data acquired from a variety of sources, and the embodiments of the invention are not limited to the sources listed herein. For example, the data may be acquired by stereoelectroencephalography (SEEG). The systems and methods described herein can also be applied to electrocorticography recordings, as well as any type of invasive electroencephalogram (EEG) recordings, for example, SEDD, electrocortocography (ECoG). The systems and methods described herein can be applied to scalp EEG, magnetoencephalography (MEG), and functional magnetic resonance imaging (FMRI) readings, for example.

A Computational Tool to Characterize the EZ

Figure 2:
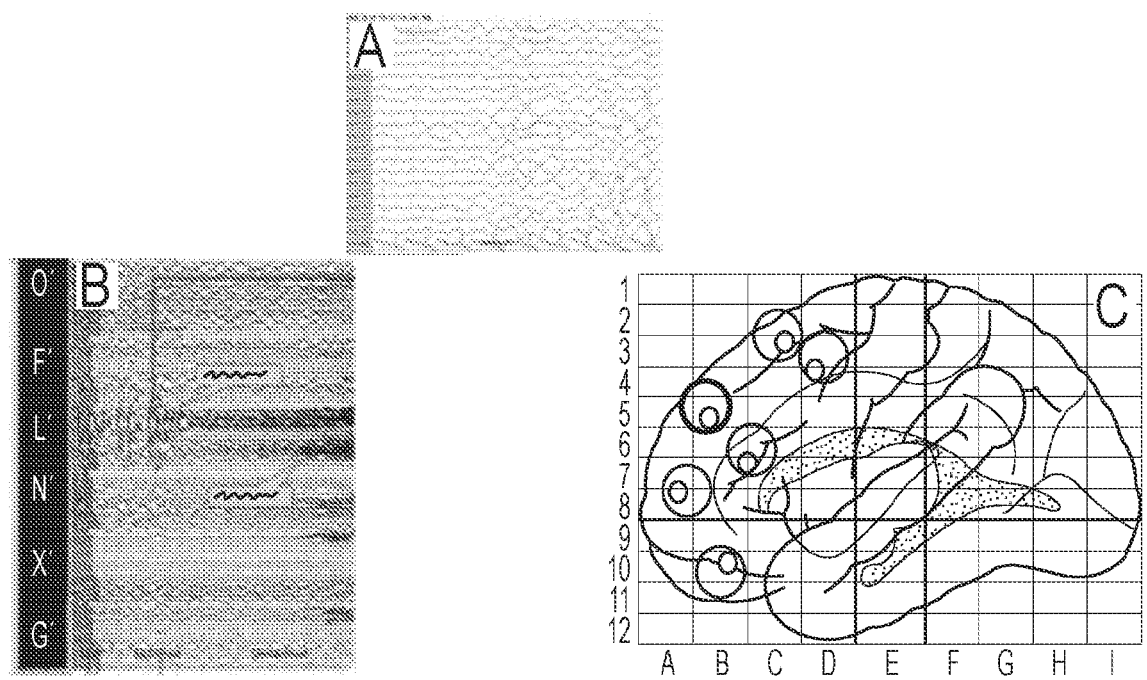
FIG. 2 shows the clinical-anatomo-functional analysis with generation of individualized epileptic network roadmaps in a patient with MRE and non-lesional MRI. A. Clinical semiology suggesting left frontal seizures. B. Scalp SEEG showing interictal spikes in the left frontal regions. C. Anatomo-Functional SEEG analysis showing the EN and its components: seizure onset zone (bold red circle) located in electrode L' with early and late spread zones (light red circles) in electrodes N' and F'. Final representation of the EN using the Talairach coordinates.

Departing from the more traditional focal concept, epileptic activity can be interpreted as a network phenomenon characterized by seizures caused by hypersynchronous activity of populations of neurons at the cortical and subcortical levels, which are anatomically organized in distant nodes and pathways that together, compose the EZ (FIG. 2). In previous work, a seizure event was defined as an instability phenomenon of a dynamic networked system [56]. Specifically, it was argued that the cortical network in epilepsy is on the brink of instability, and that small perturbations to functional connections between populations of neurons (network nodes) render the stable network unstable, causing a seizure. Fragility of each network node was defined and computed for different network models [56].

The systems and methods according to some embodiments of the invention correlate the most fragile nodes of a network to the EZ. The systems and methods can be used to (i) estimate linear models from recordings obtained from, for example, SEEG, ECoG, scalp EEG, or other modality; (ii) compute the fragility of each electrode contact (network node) from the models; and (iii) assign a weight to each electrode sorted by the most fragile electrodes derived from the models to the least fragile. The weights can be visualized via a heatmap overlayed on the patient's brain image, though other methods of visualizing the weights are also possible. We found that the most fragile nodes of the epileptic network in patients have a high degree of agreement with clinically annotated EZs for those patients. Data are presented below.

The systems and methods according to some embodiments of the invention use an algorithm that processes intracranial or stereoEEG data recorded from epilepsy patients and generates a heatmap that identifies the epileptogenic zone (EZ) with minutes of data. The systems and methods can identify the EZ before seizures occur and in minutes in an automated fashion. All known algorithms require data from seizures, and thus rely on patients to stay in the hospital until seizures occur. The longer the patient is being monitored with electrode implantation, the higher the risk of infection. The systems and methods described herein mitigate that risk by identifying the EZ using data acquired before a seizure occurs.

In this section, the notion of network nodal fragility is described as introduced in the context of SEEG recordings [56]. Then, the application of the fragility theory to models constructed from SEEG data to identify the EZ is described. However, the embodiments of the invention are not limited to processing SEEG data, but can be applied to any type of data from a patient's brain.

Fragility of Network Nodes

Before delving into some mathematics, one may consider a social network wherein each node is a person and people are connected by edges if they are friends with one another, weighted by the strength of the friendship. Suppose one is interested in understanding how a rumor could spread throughout the network assuming that each person has some probability of telling his/her friends the rumor if he/she hears it. It is also assumed that the rumor starts in a "private" network where rumors spread with low probability. That is, when a person hears some gossip, they may tell their friends, but the network connectivity is such that the rumor has a very low probability of spreading. The fragility question then is: "how much do the friendships of a specific person need to be strengthened or weekend (perturbing a specific node's connection weights) such that the rumor spreads like wildfire (i.e., high probability)?" If the person's connections must be changed significantly to spread a rumor, then that person is not a fragile node in the network. On the other hand, if tiny perturbations to a person's connection strengths cause a rumor to spread, then that person is a very fragile node in the network.

The analogy made herein to epileptic networks is as follows: "how much do the functional connections between populations of neurons (as measured by SEEG) need to be changed to enable the network to have seizures (rumor spread)?" To answer this question quantitatively, some notation and basic stability theory of linear networked systems are introduced. Let each time series recording from SEEG channel i be denoted as $x_1(t)$ and let $x_i(t)$ be the vector of n channel recordings for i=1, 2, . . . , n. It is assumed that the SEEG recordings for a given patient evolve in a linear fashion as follows:

$$x(t+1) = Ax(t) \quad (1.1)$$

for t=1, 2, 3, . . . millisecond is some fixed window in time T (e.g. T=500 msec). Equation (1.1) is a model for a discrete time linear system where x(t) is called the state vector and $A \in R^{n \times n}$ is called the "state transition" matrix. The state transition matrix can be viewed as an adjacency matrix representation of the functional connectivity of a network of n nodes, whose dynamics are linear and captured in the evolution of the state vector. Element $A_{ij}$ indicates how the activity of node j, $x_j(t)$, affects the future activity of node i, $x_i(t+1)$. Element $A_{ij}$ is an autofeedback term, representing a first-order approximation to the internal dynamics of node i. More generally, the $i^{th}$ row of A dictates the network's cumulative functional effect on node i, while the $j^{th}$ column captures the functional effect of the activity of node j on the entire network.

From linear systems theory, the system is said to be asymptotically stable about a fixed point, $\bar{x}$ if x(t) converges to $\bar{x}$ as t→∞ for all initial conditions. This implies that the activity of the nodes remains at a baseline value and responds transiently to external inputs before recovering. In terms of the matrix representation (2), stability is equivalent to the eigenvalues of A (with eigenvalues $\lambda_1 \ldots \lambda_n \in C$) being inside the unit disk in the complex plane, i.e., $|\lambda_i|<1$, i=1, 2, . . . , n. The system is said to be marginally stable if any eigenvalue is on the unit disk, $|\lambda_i|=1$, which means that given some initial condition x(0), the network will oscillate (seen in SEEG recordings during seizures).

The systems and methods according to some embodiments of the invention rely on the principle that a seizure event occurs when a stable network system transitions to an unstable system via small perturbations in connection weights to one or more nodes. Network fragility is defined as the magnitude of the minimum energy perturbation exerted by Δ on A that is required to push the network to the brink of instability (new system after perturbation has transition matrix is A+Δ). If a large magnitude perturbation to each node is required, the network is more robust, while small energy perturbations correspond to a fragile network. Solving for the smallest Δ entails minimizing over real matrices such that the dynamical system has eigenvalues that move outside the unit disk. Mathematical details are provided in [56].

Figure 3:
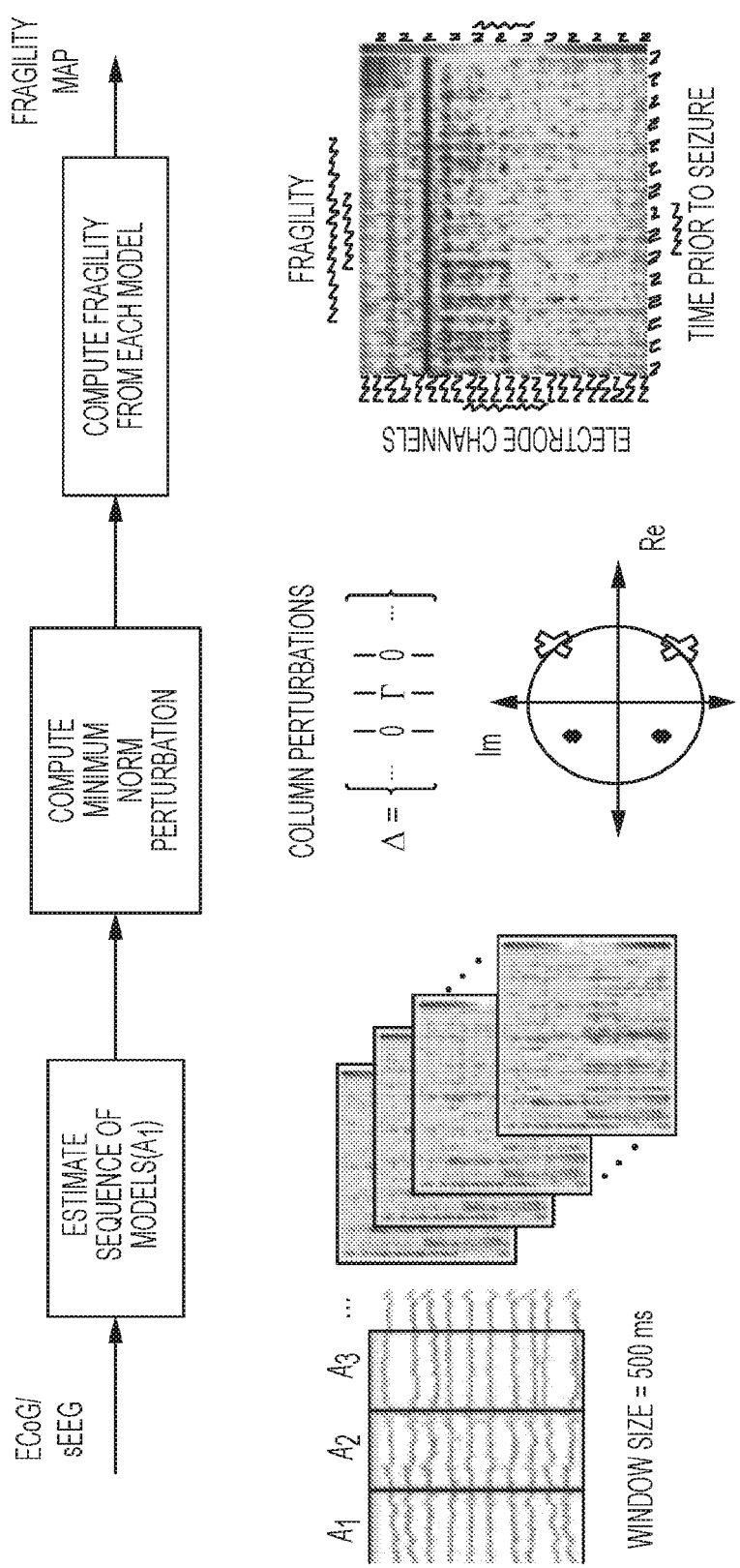
FIG. 3 shows computational steps of EZTrack according to some embodiments.

According to some embodiments of the invention, EZTrack comprises three computational steps: (i) constructing models from SEEG, ECog, scalp EEG, or other types of data over a time period before seizure onset using least squares estimation [78] (a sequence of matrices computed for subwindows of size describing evolution of SEEG data every second), (ii) computing a minimum norm perturbation of each channel from each model, and (iii) computing fragility for each channel to track each node's fragility leading to seizure onset. This fragility may be converted into a weight ranging from 0 to 1. FIG. 3 shows a schematic of EZTrack. The channels whose weights are above a threshold a constitute EZTrack's EZ, denoted as EEZ. The EEZ can be compared to clinically annotated EZ (CEZ), and the parameters {W, T, α} can be adjusted and optimized.

Preliminary Results

Figures 4, 5A, 5B, 5C:
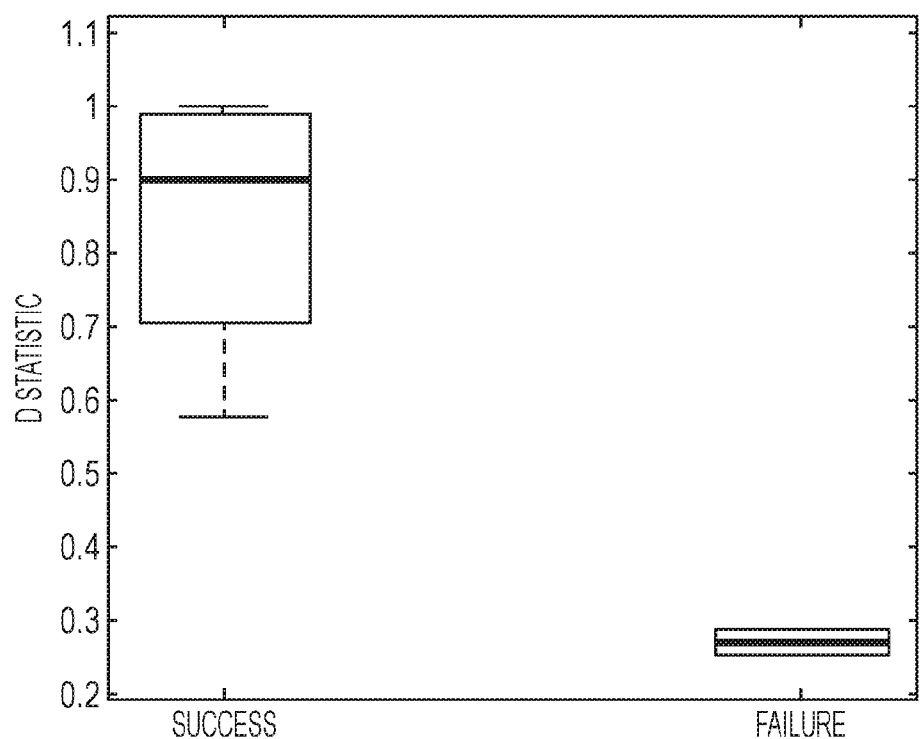
FIG. 4 shows preliminary results (D statistics vs surgical outcome).
FIG. 5A shows perturbation topologies in $R^{N \times N}$, where diagonal perturbations only disrupt autofeedback terms.
FIG. 5B shows perturbation topologies in $R^{N \times N}$, where column perturbations have non-zero entries in a single column.
FIG. 5C shows perturbation topologies in $R^{N \times N}$, where row perturbations have a single row with non-zero entries.

For {W=60 sec, T=500 msec, α=0.8}, we tested EZTrack on 6 SEEG patients treated at the Cleveland Clinic and 4 ECoG patients treated at JHU with surgical resections. FIG. 4 plots the DOA distributions for each outcome.

Clinical standard for identifying the EZ

Initially, by analyzing the available non-invasive data and the temporal evolution of the epileptic clinical manifestations, an individual anatomo-electro-clinical hypothesis of the EZ and the more extensive epileptic network is formulated. The SEEG implantation plan is created by experienced epileptologists, neurosurgeons and neuroradiologists who, together, formulate an implantation strategy. The formulated implantation strategy takes into account the 3D aspects of depth electrode recordings, which despite a limited coverage of the cortical surface, enable an accurate sampling of the structures along its trajectory, from the entry site to the final target point. After extensive clinical analysis of video-SEEG data, the volumetric MRIs of each patient are co-registered to a common work space (T1 volumetric MRI), and the electrode contacts (retrieved from post-implantation CTs) from each patient are fully warped into the digital space. The combined anatomical position of the electrode contacts are then grouped initially by standard clinical nomenclature as part of the epileptic network and its temporal-spatial subdivisions [seizure onset zone (SOZ), early propagation zone (EPZ) and late propagation zone (LPZ)], based on the anatomo-electro-clinical seizure correlations during the SEEG recordings phase (FIG. 2). Specifically, the EZ corresponds to the nodes demonstrating the earliest electrophysiological changes (SOZ) and the nodes involved at the time of the earliest clinical manifestations (EPZ). (FIG. 2).

The following examples describe some further concepts of the invention with reference to particular examples. The general concepts of the current invention are not limited to the particular examples.

EXAMPLES

Currently, there are two surgical and potentially curative treatment options for focal MRE: (i) surgical removal of the EZ (oldest, most common and well-established treatment), and (ii) electrical stimulation of the EZ [80].

Despite the fact that successful treatment is life changing, surgical treatment utilization is minimal (only 2%) because the clinical workflow to localize the EZ can be interpreted by referring physicians and patients as excessive, invasive, long, complex, expensive and fraught with problems: (i) there is low efficiency in EZ localization, (ii) the patient endures a prolonged hospital stay, risking infection and neurological comorbidities as the clinician waits for several seizure events to accrue sufficient data, (iii) specialized clinicians manually inspect individual EEG "channels" to localize the EZ. Since it is extremely difficult to interpret recordings by eye, quantitative methods such as ours can help in localizing the EZ more efficiently, reducing hospital stays and assist clinicians in decision making. After localization is completed, the predicted EZ and surrounding regions are typically "openly" resected through a craniotomy approach. Despite large brain regions being removed, surgical success rates barely reach 60-65% [12, 17,81-83]. Such variable and disappointing outcomes associated with high morbidity rates are often due to imprecise and/or inaccurate localization of the EZ in association with high invasiveness in the current diagnosis and treatment modalities.

The notion of network nodal fragility is described as introduced in [56]. Then the application of the fragility theory according to some embodiments to models constructed from patient data to identify the EZ is described.

A. Fragility of Network Nodes

Consider a discrete time linear system with state evolution equation as (2.1) with state vector $x(t) \in R^N$, and state transition matrix $A \in R^{N \times N}$ with eigenvalues $\lambda_1 \ldots _N \in C$ where $|\lambda_1| \geq \ldots \geq |\lambda_N|$.

$$x(t+1) = Ax(t). \tag{2.1}$$

The state transition matrix can be viewed as an adjacency matrix representation of the functional connectivity of a network of N nodes, whose dynamics are linear and captured in the evolution of the state vector. The elements in the state vector are some metric of the activity of each node. Element $A_{ij}$ indicates how the activity of node j, $x_j(t)$, affects the future activity of node i, $x_i(t+1)$. Element $A_{ii}$ is an autofeedback term, representing a first-order approximation to the internal dynamics of node i. More generally, the $i^{th}$ row of A dictates the network's cumulative functional effect on node i, while the $j^{th}$ column captures the functional effect of the activity of node j on the entire network.

From linear systems theory, the system is said to be asymptotically stable about a fixed point, $\bar{x}$, if x(t) converges to $\bar{x}$ as $t \to \infty$ for all initial conditions. This implies that the activity of the nodes remains at a baseline value and responds transiently to external inputs before recovering. In terms of the matrix representation, stability is equivalent to the eigenvalues of A being inside the unit disk in the complex plane, i.e., $|\lambda_i| < 1$ for all i=1, 2, ... N.

This is more evident when equation (2.1) is cast in modal form as shown in equation (2.2) where $c_i \in C$ are set according to initial conditions and $v_i \in C^N$ are the eigenvectors of A corresponding to $\lambda_i$. Assume the system has already been transformed so the fixed point is at the origin ($\bar{x}=0$) and that there are n distinct eigenvalues of A. Then the solution to the linear system can be written as:

$$x(t) = \Sigma_{i=1}^N c_i |\lambda_i|^t v_i \tag{2.2}$$

If $|\lambda_1| < 1$, the real components of the other eigenvalues are also negative by virtue of their ordering, and all the terms in (2.2) decay so that the system settles to its baseline activity (transformed to be at the origin). If $\lambda_1 = 0$, then the other eigenvalues have negative real components and their corresponding terms vanish over time, so the state settles somewhere along the first eigenvector based on initial conditions: $x(t) \to c_1 v_1$. Therefore, the network gets stuck in some pattern of activity instead of decaying to its baseline. If the elements in the state vector represent spiking rates, this may be analogous to tonic spiking or silenced neurons. Finally, if $\lambda_{1,2} = \pm j\omega$, then for large t, the activity of each node oscillates around its baseline without ever decaying. This may be a suitable representation for spiking rates entrained to an oscillation.

A linear system becomes unstable if there is a change to the state matrix so that the stability conditions on the eigenvalues are no longer met. This change can be modeled as an additive perturbation, $\Delta$, to the state matrix so that $A+\Delta$ replaces A in the state equation, (2.1), to give (2.3).

$$x(t) = (A+\Delta)x(t) \tag{2.3}$$

This notion of instability can be adopted for networks whose dynamics are linear or can be approximated as linear in some regime. For such networks, the eigenvalues of the functional connectivity matrix determine the stability properties.

A variety of perturbation matrices in (2.3) can push the original network in (2.1) into instability. Based on the structure of the perturbation (e.g., $\Delta \in R^{N \times N}$ or $\Delta \in \text{diag}\{R^N\}$ as in FIG. 5A), and which elements are preferentially affected, different perturbation strengths (measured by a matrix norm) are required to cause the perturbed system to become unstable. Network fragility is defined here as the magnitude of the minimum energy perturbation required to push the network to the brink of instability. If a large magnitude perturbation is required, the network is more robust, while small energy perturbations correspond to a fragile network. The elements that are modified by the minimum energy perturbation define the edges of the most fragile subnetwork.

Whole network perturbations or diagonal perturbations will not be considered because they are biologically unlikely. It is improbable that a whole host of functional network connections need to be modified to cause aberrant behavior or that changes in autofeedback occur in different neurons independently and in isolation without affecting functional connectivity in any other way.

Network fragility will therefore be derived for row perturbations (see FIG. 5C) corresponding to changes in the effect of incoming projections to a single neuron or population. Row perturbations may be a plausible perturbation structure to reflect anomalies in a neuron or population that affects how it integrates inputs. The column perturbation case can be derived similarly [56].

B. Network Fragility as a Structured Perturbation Problem

In this section, we reproduce from (2.1) the structured row perturbation problem formulation and solution for a discrete time linear system.

1) Theorem: Suppose $A \in R^{N \times N}$ represents the state transition matrix of a stable linear network. Then the minimum 2-induced norm additive row perturbation, $\hat{\Delta} \in \Lambda_r = e_k \Gamma^T$ and $\Gamma \in R^N$, that will destabilize the linear network (or more precisely place an eigenvalue of $A+\hat{\Delta}$ at $\lambda = \sigma + j\omega$, $-1 < \omega \leq 1$), is given by $$\hat{\Delta} = e_k [B^T(BB^T)^{-1}b]^T \quad (2.4)$$

where $$B(\sigma, \omega, \hat{k}) = \begin{bmatrix} \text{Im}\{e_{\hat{k}}^T(A-(\sigma+j\omega)I)^{-T}\} \\ \text{Re}\{e_{\hat{k}}^T(A-(\sigma+j\omega)I)^{-T}\} \end{bmatrix} \quad (2.5a)$$

$$b = \begin{bmatrix} 0 \\ -1 \end{bmatrix} \quad (2.5b)$$

and $\hat{k}$ is the row where the perturbation is applied. $e_k \in R^N$ is the $k^{th}$ elementary basis vector.

2) Proof $$\hat{\Delta} = \underset{\Delta \in \Lambda_{r,\omega}}{\operatorname{argmin}} \|\Delta\|_2 \mid \exists i: \lambda_i(A+\Delta) = \sigma + j\omega, \quad (2.6)$$

$$\forall i: |\lambda_i(A)| < 1, i \in 1 \ldots N, A \in R^{N \times N}\}$$

Since $\sigma + j\omega$ is an eigenvalue of $A+\Delta$, $\exists v \in C^N$, $v \neq 0$ such that $(A+\Delta)v = \sigma + j\omega v$ (2.7a)

$(A+e_k \Gamma^T)v = \sigma + j\omega v$ (2.7b)

$(A+e_k \Gamma^T - (\sigma+j\omega)I)v = 0$ (2.7c)

Let $|\bullet|$ denote the determinant. From the characteristic equation, $|A-(\sigma+j\omega)I + e_k \Gamma^T| = 0$ (2.8)

Since $\Delta_i(A) \neq (\sigma+j\omega)$, $|A-j\omega I| \neq 0$ and $(A-j\omega I)^{-1}$ exists, so (8) can be factored as $|(A-(\sigma+j\omega)I)(I+(A-(\sigma+j\omega)I)^{-1}e_k \Gamma^T)| = 0$ (2.9)

Recall that $|AB| = |A||B|$.

$|(A-(\sigma+j\omega)I)||(I+(A-(\sigma+j\omega)I)^{-1}e_k \Gamma^T)| = 0$ (2.10a)

$|I+(A-(\sigma+j\omega)I)^{-1}e_k \Gamma^T| = 0$ (2.10b)

For conformable matrices C and D, $|I-CD| = |I-DC|$ so $|1+\Gamma^T(A-(\sigma+j\omega)I)^{-1}e_k| = 0$ (2.11a)

$\Gamma^T(A-(\sigma+j\omega)I)^{-1}e_k = -1$ (2.11b)

Equation (2.11b) also holds if $\sigma+j\omega$ is replaced by $\sigma-j\omega$ (by taking the complex conjugate of both sides) as expected. Since $A+\Delta$ is a real matrix, its complex eigenvalues must exist in conjugate pairs with the same r necessarily producing both. Now define $a(\omega, \sigma, k) = (A-(\sigma+j\omega)I)^{-1}e_k$ (2.12a)

$a_i(\omega, \sigma, k) = \text{Im}\{a(\omega, \sigma, k)\}$ (2.12b)

$a_r(\omega, \sigma, k) = \text{Re}\{a(\omega, \sigma, k)\}$ (2.12c)

By definition of the induced 2-norm, $\|\Delta\|_2 = \max\{\|\Delta x\|_2 | x \in R^N, \|x\|_2 = 1\}$ (2.13)

Since $\|\Delta\|_2 = \|\Delta^T\|_2$ and only the $k^{th}$ column of $\Delta^T$ is nonzero, the maximum is achieved for $x = e_k$.

$\|\Delta^T\|_2 = \|\Delta^T e_k\|_2$ (2.14a)

$= \|\Gamma e_k^T e_k\|_2$ (2.14b)

$= \|\Gamma\|_2$ (2.14c)

Then, using (2.11b), (2.12b) and (2.12c), an equivalent minimization is $$\min_{\Delta \in \Lambda_r, \omega, \sigma} \|\Delta\|_2 \Leftrightarrow \min_{0 < \omega \leq \omega_0, k} \left\{\|\Gamma\|_2 \left| \begin{bmatrix} a_i^T(\omega, \sigma, k) \\ a_r^T(\omega, \sigma, k) \end{bmatrix} \Gamma = \begin{bmatrix} 0 \\ -1 \end{bmatrix} \right. \right\} \quad (2.15)$$

This is just an underdetermined least squares problem over $\omega$, $\sigma$, and k where $\omega_0$ is the upper bound of the frequency range within which to search. Then the minimum magnitude $\Gamma$ is achieved at $(\hat{w}, \hat{\sigma}, \hat{k})$, and $\hat{\Delta} = e_{\hat{k}} \hat{\Gamma}^T$.

$\hat{\Gamma} = B^T(BB^T)^{-1}b$ (2.16)

If $\omega=0$, then $a_i(\omega, \sigma, k) = 0$ so the first condition in (2.15) needs to be omitted, and $\Gamma$ simplifies to the expected form.

$$\Gamma = \frac{-a_r}{a_r^T a_r} = \frac{-a}{a^T a} \quad (2.17)$$

More generally, these results can be extended to ensure certain elements remain unperturbed within a row or column by including additional orthogonality constraints in (2.15) to the corresponding elementary basis vectors.

C. Model Estimation and Computation of Network Fragility

In this study, we applied the perturbation theory of discrete time network fragility above to identify the seizure onset zone in two MRE patients using intracranial EEG data recorded at a 1 kHz sampling rate. The recordings are described in more detail in section II-E. Each patient had N electrodes implanted with usable data. Data from 60 seconds prior to seizure to seizure onset was used. A sliding window of 500 ms with a step size of 500 ms (no overlap) was then moved over this period. For a period of 60 seconds till seizure onset, this constitutes 120 windows, with a generated A matrix for each window.

The process proceeds as follows: For each 500 ms window, we constructed a discrete-time linear time invariant model (of the form equation (2.1)) from the intracranial EEG recordings, which led to a sequence of models $\{A_j\}$ for j=1, 2, ..., 120. Specifically, each recording from electrode i was considered a realization of a state variable $x_i(t)$ for i=1, 2, ..., N assumed to be generated by model $x(t+1)=A_j x(t)$ for $t \in [500(j-1), 500j]$. Each state evolution matrix $A_j$ was estimated by minimizing the squared error between the data and the model. That is, $\|x(t)-\hat{x}(t)\|_2$ was minimized over $A_j$ such that $\hat{x}(t+1)=A\hat{x}(t)$.

The following variables describe an example window of data. The embodiments of the invention are in no way limited to these values.

T=window size (500 ms)
N=number of electrodes
$b \in R^{(T-1)N}$, where b are the electrode recordings at the next time point
$H \in R^{(T-1)N \times N^2}$
$A \in R^{N \times N}$, where A is the vectorized adjacency matrix we are interested in
$x_i(t)$, t=1, 2, ..., T, are the iEEG time series from each window of electrode i The model for the adjacency matrix is constructed by transforming the data and unknowns into a linear system of equations: b=HX, and then solving the least squares problem in MATLAB using X=H\b. The following system of linear equations comes directly from writing out the recursion of the LTI model for each time step:

$$x_1(2) = A_{1,1}x_1(1) + A_{1,2}x_2(1) + \ldots + A_{1,N}x_N(1)$$
$$x_2(2) = A_{2,1}x_1(1) + A_{2,2}x_2(1) + \ldots + A_{2,N}x_N(1)$$
$$\vdots$$
$$x_N(2) = A_{N,1}x_1(1) + A_{N,2}x_2(1) + \ldots + A_{N,N}x_N(1)$$
$$x_1(3) = A_{1,1}x_1(2) + A_{1,2}x_2(2) + \ldots + A_{1,N}x_N(2)$$
$$x_2(3) = A_{1,1}x_1(2) + A_{1,2}x_2(2) + \ldots + A_{1,N}x_N(2)$$
$$\vdots$$
$$x_1(T) = A_{1,1}x_1(T) + A_{1,2}x_2(T) + \ldots + A_{1,N}x_N(T)$$
$$\vdots$$
$$x_N(T) = A_{N,1}x_1(T) + A_{N,2}x_2(T) + \ldots + A_{N,N}x_N(T)$$

The model matrices are constructed as s such and solved for each window.

$$b = [x_1(2) \; x_2(2) \ldots x_N(2) \ldots x_1(T) x_2(T) \ldots x_N(T)]^T$$

$$H = \begin{bmatrix} x_1(1) \ldots x_N(1) & 0 \ldots 0 & 0 \ldots 0 \\ 0 \ldots 0 & x_1(1) \ldots x_N(1) & 0 \ldots 0 \\ 0 \ldots 0 & 0 \ldots 0 & x_1(1) \ldots x_N(1) \\ \ldots & \ldots & \ldots \\ x_1(2) \ldots x_N(2) & 0 \ldots 0 & 0 \ldots 0 \\ \ldots & \ldots & \ldots \\ 0 \ldots 0 & 0 \ldots 0 & x_1(2) \ldots x_N(2) \\ \ldots & \ldots & \ldots \\ x_1(T) \ldots x_N(T) & 0 \ldots 0 & 0 \ldots 0 \\ \ldots & \ldots & \ldots \\ 0 \ldots 0 & 0 \ldots 0 & x_1(T) \ldots x_N(T) \end{bmatrix}$$

$$X = [A_{11} \; A_{12} \ldots A_{1N} \; A_{21} \ldots A_{N,N-1} \; A_{NN}]^T$$

After solving for X, it can be reshaped into a matrix A. For each estimated $A_j$, we then computed the minimum norm perturbation $\Gamma_j$ for a row perturbation and the corresponding fragility metric $\|\hat{\Delta}_j\|_k$ at each node k=1, ..., N. The fragility metric is computed as:

j=1, ..., 120, is the time indice.

k-1, ..., N, is the electrode indice.

$\|\hat{\Delta}_j\|_k = (\max(\Gamma_j) - \Gamma_{jk})/\max(\Gamma_j)$

With the estimated minimum norm perturbation for each channel at each time window, the iEEG time series data can be used to determine fragility changes of each electrode over time. For each time window j, we have N values of fragility, one for each electrode k. We form a fragility matrix F as follows:

$$F = \begin{bmatrix} \|\hat{\Delta}_1\|_1 & \|\hat{\Delta}_2\|_1 & \ldots & \|\hat{\Delta}_{120}\|_1 \\ \|\hat{\Delta}_1\|_2 & \|\hat{\Delta}_2\|_2 & \ldots & \|\hat{\Delta}_{120}\|_2 \\ & & \vdots & \\ \|\hat{\Delta}_1\|_N & \|\hat{\Delta}_2\|_N & \ldots & \|\hat{\Delta}_{120}\|_N \end{bmatrix}$$

D. EZ Identification Using Network Fragility

The EZ is identified using the model by applying a threshold to each element of F. A threshold of 0.8 was used for the fragility metric. This converts the F matrix into a matrix of 0's and 1's, and the rowsum of this resulting matrix will give a weight toward each electrode. This is ranked and produces a clinical heatmap that is compared with the heatmap produced by clinicians. Note that many electrodes may have weights of 0; the electrodes will not be considered as candidates for the EZ.

Figure 6A:
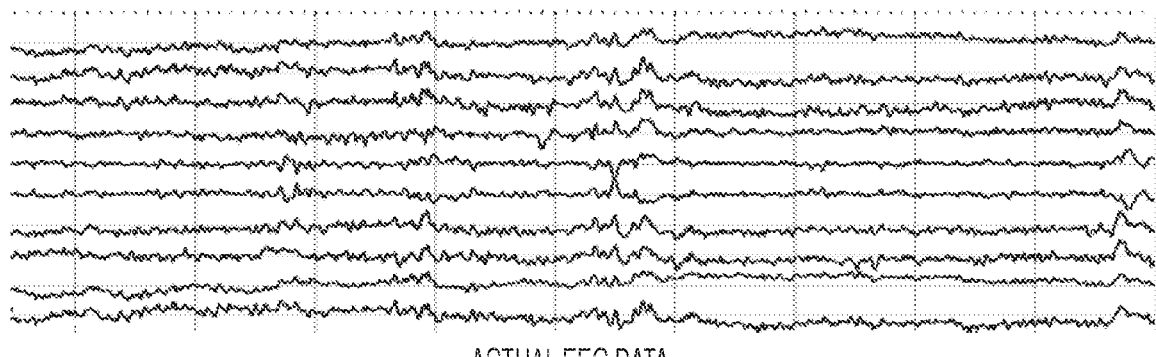
FIG. 6A shows actual EEG data.
Figure 6B:
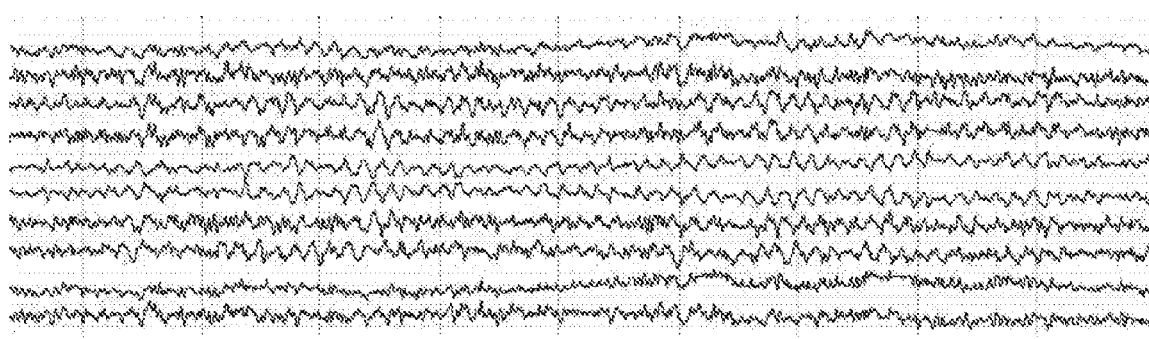
FIG. 6B shows simulated EEG data corresponding to FIG. 6A. This figure shows simulated data generated from the discrete linear time-varying model according to some embodiments of the invention.

To determine if the linear time-varying model is valid, a simulation of ECoG data was demonstrated using the computed A matrices. In FIGS. 6A and 6B, a window of simulation vs. real ECoG data is shown, where each $A_j$ is used to compute ECoG data. Although different, many qualitative characteristics are still preserved. It is apparent that the simulated data does not produce epileptic type behavior, but still conserves interictal type patterns.

Figure 7:
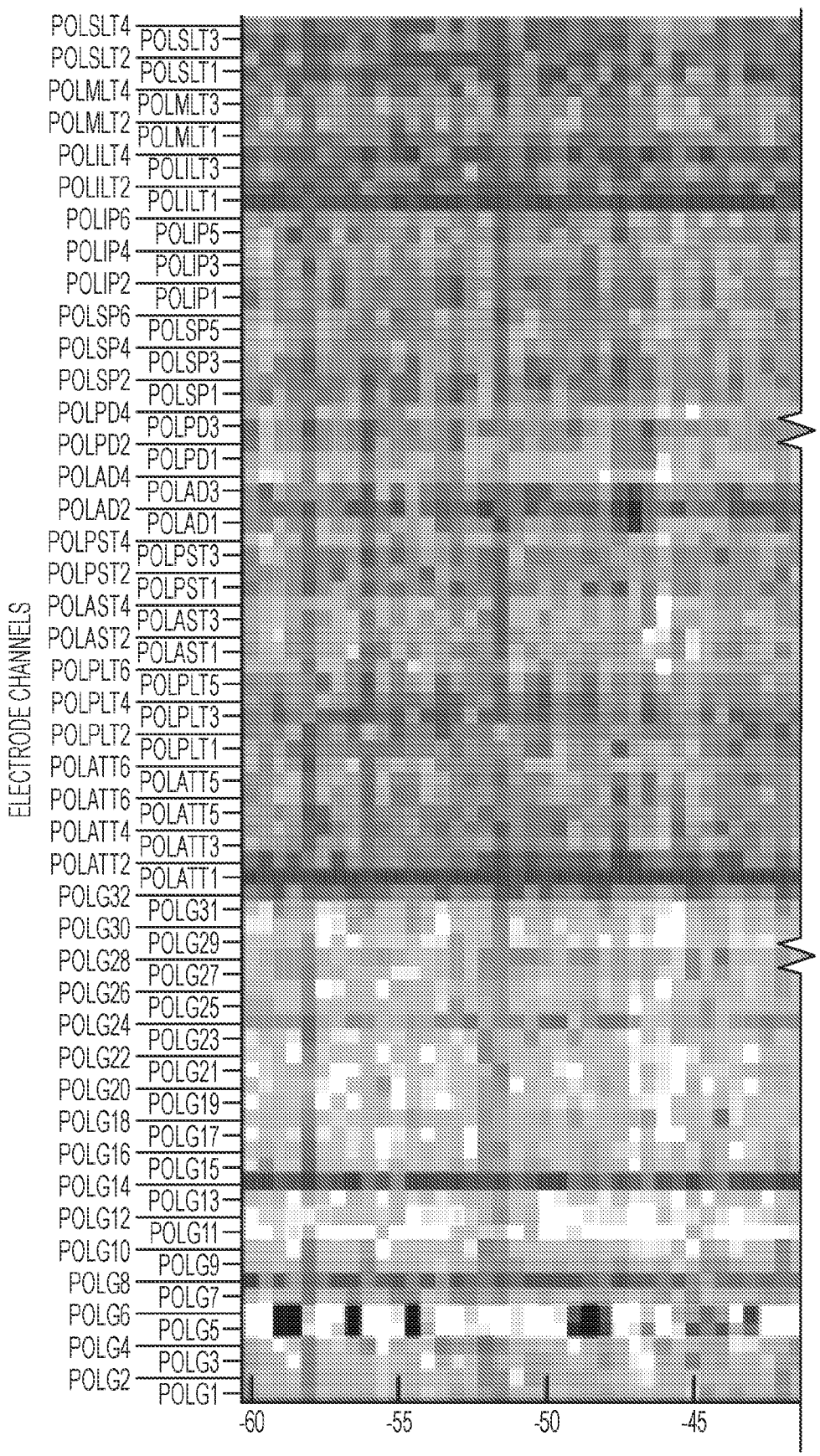
FIG. 7 shows an example of the minimum norm perturbation of electrodes over time (the F matrix). The clinically annotated EZ electrodes have rows marked by closed circles. Open circles and stars correspond to the clinically labeled early onset and late onset, respectively.
Figure 7:
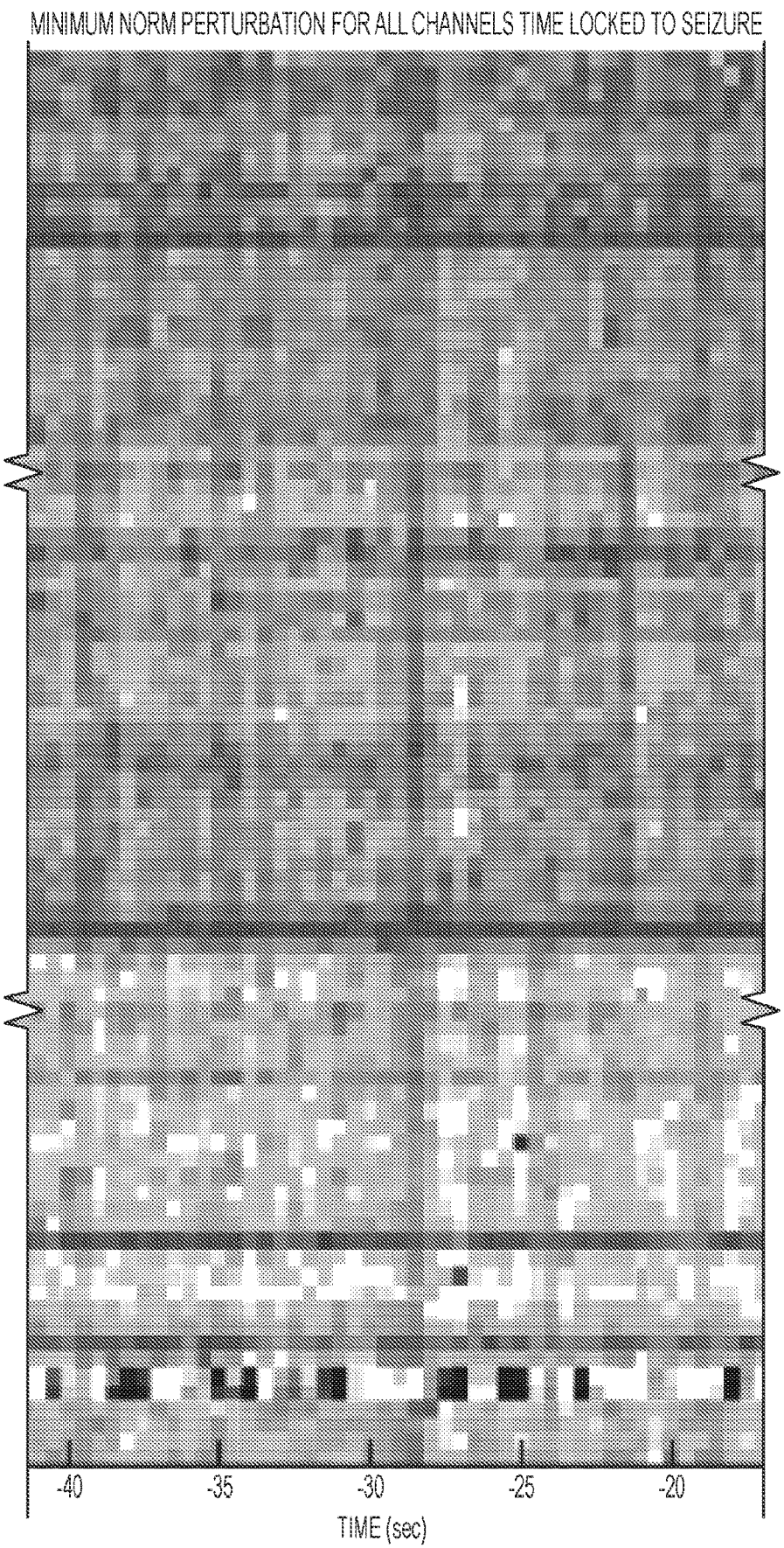
Figure 7:
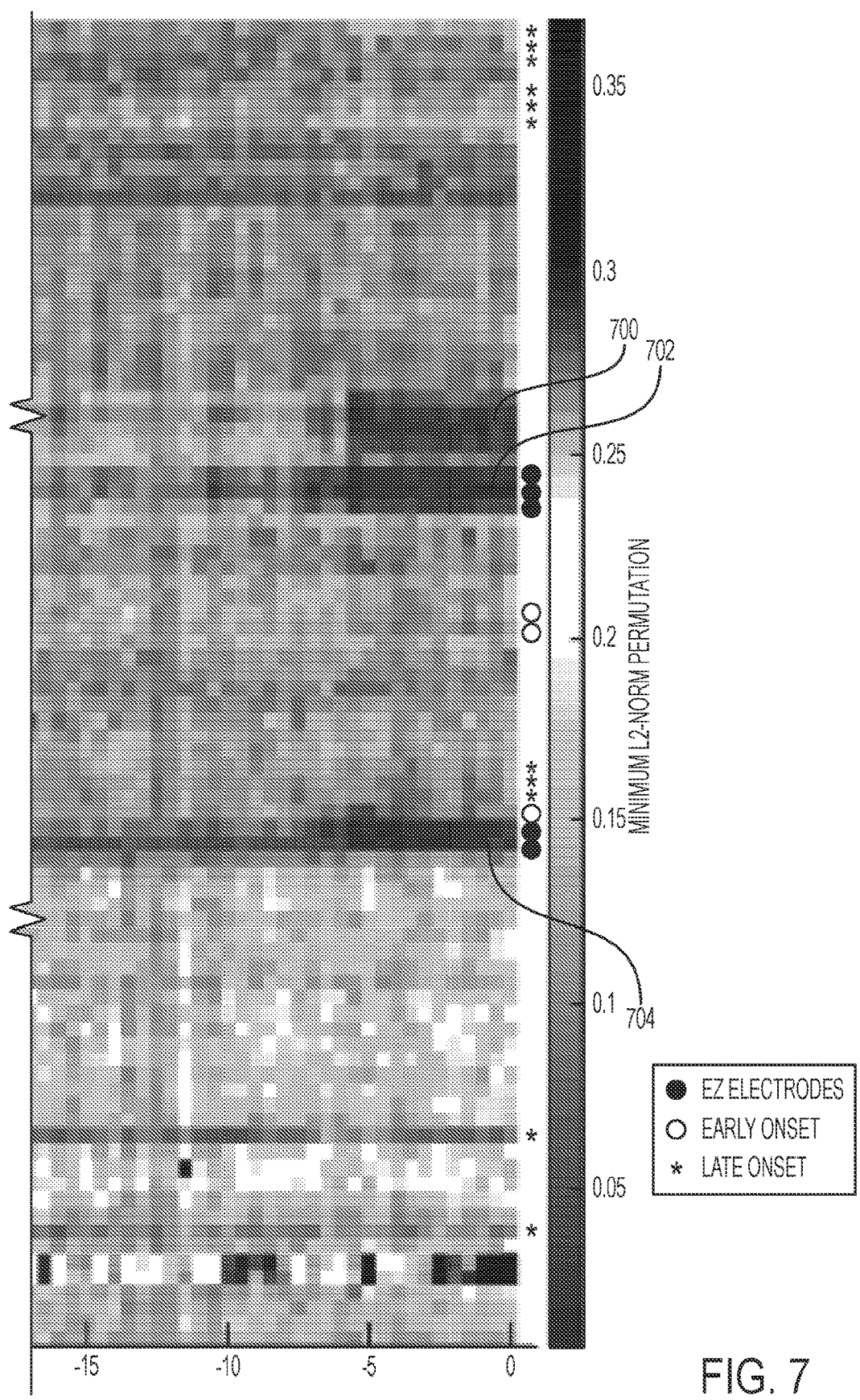

The analysis was performed on two patients, with two seizures each. First, a minimum norm perturbation matrix was computed for each dataset. An example of the minimum norm perturbation matrix is shown in FIG. 7. The minimum norm perturbation matrix may also be referred to as a "fragility map." The fragility map indicates the relative fragility of each electrode at each point in time. In the example in FIG. 7, the fragility map indicates the relative fragility for each electrode for a 60 second period before onset of a seizure at Time=0 sec. For certain electrodes, in a time period before seizure onset, the minimum perturbation necessary for instability becomes significantly lower (see the regions 700, 702, and 704). In some embodiments, color is used to indicate the relative fragility in the fragility map.

From these matrices, all the F matrices were computed. Most of the electrodes in the clinically annotated EZ show either a consistent fragile state, or a transition into a fragile node at some time, around 10 seconds before seizure. The analysis also seems to be consistent across two different seizures for each patient.

With a fragility matrix for each patient, for each seizure, the electrodes can be weighted in order of most fragile to least fragile. The most fragile nodes in this analysis correspond to fragile nodes from a row perturbation. The clinical interpretation is that these electrodes cover a neural region that easily renders the epileptic network unstable when neural inputs to that region are perturbed. In general, this method correctly ranks the clinically annotated electrodes as the most fragile nodes.

The electrodes in the early and late spread onset show some degree of fragility, or transition into fragility close to seizure onset. However, the qualitative characteristics are not as strong. When computed into electrode weights, these electrodes are not apparent in the clinical heatmaps.

Herein, seizures are characterized as periods during which a time varying dynamical network system goes unstable. The most fragile nodes of an epileptic network may correspond to the region of the brain that starts seizures, defined as the epileptogenic zone (EZ). The derivation of nodal fragility introduced in (56) is used and applied to electrocorticographic (ECoG) recordings obtained from epilepsy patients being monitored for clinical purposes. Linear time varying models are estimated from the ECoG recordings in a window of 60 seconds prior to seizure onset. The most fragile nodes (ECoG channels) are then computed from the models. It was found that the most fragile nodes that destabilize the epileptic cortical network in each patient have a high degree of concordance with the clinical annotations and can thus be used to help identify the EZ, which currently is a difficult, costly and time-consuming process.

REFERENCES

1. Brodie M J, Shorvon S D, Canger R, et al. Commission on European Affairs: appropriate standards of epilepsy care across Europe.ILEA. Epilepsia. 1997; 38(11):1245-1250.
2. Berg A T, Kelly M M. Defining intractability: comparisons among published definitions. Epilepsia. 2006; 47(2): 431-436.
3. Kwan P, Brodie M J. Definition of refractory epilepsy: defining the indefinable? The Lancet. Neurology. 2010; 9(1):27-29.
4. Murray M I, Halpern M T, Leppik I E. Cost of refractory epilepsy in adults in the USA. Epilepsy research. 1996; 23(2):139-148.
5. Begley C E, Famulari M, Annegers J F, et al. The cost of epilepsy in the United States: an estimate from population-based clinical and survey data. Epilepsia. 2000; 41(3):342-351.
6. Begley C E, Durgin T L. The direct cost of epilepsy in the United States: A systematic review of estimates. Epilepsia. 2015; 56(9):1376-1387.
7. Ferro M A, Speechley K N. Stability of latent classes in group-based trajectory modeling of depressive symptoms in mothers of children with epilepsy: an internal validation study using a bootstrapping procedure. Social psychiatry and psychiatric epidemiology. 2013; 48(7):1077-1086.
8. Luders H, Schuele S U. Epilepsy surgery in patients with malformations of cortical development. Current opinion in neurology. 2006; 19(2):169-174.
9. Hermann B P, Seidenberg M, Dow C, et al. Cognitive prognosis in chronic temporal lobe epilepsy. Annals of neurology. 2006; 60(1):80-87.
10. Najm I M, Naugle R, Busch R M, Bingaman W, Luders H. Definition of the epileptogenic zone in a patient with non-lesional temporal lobe epilepsy arising from the dominant hemisphere. Epileptic disorders: international epilepsy journal with videotape. 2006; 8 Suppl 2:S27-35.
11. Rosenow F, Luders H. Presurgical evaluation of epilepsy. Brain: a journal of neurology. 2001; 124(Pt 9):1683-1700.
12. Bulacio J C, Jehi L, Wong C, et al. Long-term seizure outcome after resective surgery in patients evaluated with intracranial electrodes. Epilepsia. 2012; 53(10):1722-1730.
13. Wyllie E, Luders H, Morris H H, 3rd, et al. Subdural electrodes in the evaluation for epilepsy surgery in children and adults. Neuropediatrics. 1988; 19(2):80-86.
14. Jayakar P, Duchowny M, Resnick T J. Subdural monitoring in the evaluation of children for epilepsy surgery. Journal of child neurology. 1994; 9 Suppl 2:61-66.
15. Adelson P D, O'Rourke D K, Albright A L. Chronic invasive monitoring for identifying seizure foci in children. Neurosurgery clinics of North America. 1995; 6(3): 491-504.
16. Jayakar P. Invasive EEG monitoring in children: when, where, and what? Journal of clinical neurophysiology: official publication of the American Electroencephalographic Society. 1999; 16(5):408-418.
17. Jeha L E, Najm I, Bingaman W, Dinner D, Widdess-Walsh P, Luders H. Surgical outcome and prognostic factors of frontal lobe epilepsy surgery. Brain: a journal of neurology. 2007; 130(Pt 2):574-584.
18. Lopez-Gonzalez M A, Gonzalez-Martinez J A, Jehi L, Kotagal P, Warbel A, Bingaman W. Epilepsy surgery of the temporal lobe in pediatric population: a retrospective analysis. Neurosurgery. 2012; 70(3):684-692.
19. Widdess-Walsh P, Jeha L, Nair D, Kotagal P, Bingaman W, Najm I. Subdural electrode analysis in focal cortical dysplasia: predictors of surgical outcome. Neurology. 2007; 69(7):660-667.
20. Najm I M, Bingaman W E, Luders H O. The use of subdural grids in the management of focal malformations due to abnormal cortical development. Neurosurgery clinics of North America. 2002; 13(1):87-92, viii-ix.
21. Nair D R, Burgess R, McIntyre C C, Luders H. Chronic subdural electrodes in the management of epilepsy. Clinical neurophysiology: official journal of the International Federation of Clinical Neurophysiology. 2008; 119(1):11-28.
22. Gonzalez-Martinez J, Bulacio J, Alexopoulos A, Jehi L, Bingaman W, Najm I. Stereoelectroencephalography in the "difficult to localize" refractory focal epilepsy: early experience from a North American epilepsy center. Epilepsia. 2013; 54(2):323-330.
23. Vadera S, Mullin J, Bulacio J, Najm I, Bingaman W, Gonzalez-Martinez J. Stereoelectroencephalography following subdural grid placement for difficult to localize epilepsy. Neurosurgery. 2013; 72(5):723-729; discussion 729.
24. Lee W S, Lee J K, Lee S A, Kang J K, Ko T S. Complications and results of subdural grid electrode implantation in epilepsy surgery. Surgical neurology. 2000; 54(5):346-351.
25. Rydenhag B, Silander H C. Complications of epilepsy surgery after 654 procedures in Sweden, September 1990-1995: a multicenter study based on the Swedish National Epilepsy Surgery Register. Neurosurgery. 2001; 49(1):51-56; discussion 56-57.
26. Hamer H M, Morris H H, Mascha E J, et al. Complications of invasive video-EEG monitoring with subdural grid electrodes. Neurology. 2002; 58(1):97-103.

27. Gonzalez-Martinez J, Lachhwani D. Stereoelectroencephalography in children with cortical dysplasia: technique and results. Child's nervous system: ChNS: official journal of the International Society for Pediatric Neurosurgery. 2014; 30(11):1853-1857.

28. Gonzalez-Martinez J, Mullin J, Bulacio J, et al. Stereoelectroencephalography in children and adolescents with difficult-to-localize refractory focal epilepsy. Neurosurgery. 2014; 75(3):258-268; discussion 267-258.

29. Gonzalez-Martinez J, Mullin J, Vadera S, et al. Stereotactic placement of depth electrodes in medically intractable epilepsy. Journal of neurosurgery. 2014; 120 (3):639-644.

30. Gonzalez-Martinez J A, Srikijvilaikul T, Nair D, Bingaman W E. Long-term seizure outcome in reoperation after failure of epilepsy surgery. Neurosurgery. 2007; 60(5): 873-880; discussion 873-880.

31. Vaugier L, Aubert S, McGonigal A, et al. Neural networks underlying hyperkinetic seizures of "temporal lobe" origin. Epilepsy research. 2009; 86(2-3):200-208.

32. Thornton R, Vulliemoz S, Rodionov R, et al. Epileptic networks in focal cortical dysplasia revealed using electroencephalography-functional magnetic resonance imaging. Annals of neurology. 2011; 70(5):822-837.

33. Spiegler A, Jirsa V. Systematic approximations of neural fields through networks of neural masses in the virtual brain. NeuroImage. 2013; 83:704-725.

34. Serletis D, Bulacio J, Bingaman W, Najm I, Gonzalez-Martinez J. The stereotactic approach for mapping epileptic networks: a prospective study of 200 patients. Journal of neurosurgery. 2014; 121(5):1239-1246.

35. Lega B, Dionisio S, Flanigan P, et al. Cortico-cortical evoked potentials for sites of early versus late seizure spread in stereoelectroencephalography. Epilepsy research. 2015; 115:17-29.

36. Jirsa V K, Stacey W C, Quilichini P P, Ivanov A I, Bernard C. On the nature of seizure dynamics. Brain: a journal of neurology. 2014; 137(Pt 8):2210-2230.

37. Bonini F, McGonigal A, Wendling F, et al. Epileptogenic networks in seizures arising from motor systems. Epilepsy research. 2013; 106(1-2):92-102.

38. Wendling F, Bartolomei F, Bellanger J J, Chauvel P. Interpretation of interdependencies in epileptic signals using a macroscopic physiological model of the EEG. Clinical neurophysiology: official journal of the International Federation of Clinical Neurophysiology. 2001; 112 (7):1201-1218.

39. Bartolomei F, Wendling F, Bellanger J J, Regis J, Chauvel P. Neural networks involving the medial temporal structures in temporal lobe epilepsy. Clinical neurophysiology: official journal of the International Federation of Clinical Neurophysiology. 2001; 112(9):1746-1760.

40. Fisher R S. Therapeutic devices for epilepsy. Annals of neurology. 2012; 71(2):157-168.

41. Gonzalez-Martinez J, Najm I M. Indications and selection criteria for invasive monitoring in children with cortical dysplasia. Child's nervous system: ChNS: official journal of the International Society for Pediatric Neurosurgery. 2014; 30(11):1823-1829.

42. Talairach J, Tournoux P, Musolino A, Missir O. Stereotaxic exploration in frontal epilepsy. Advances in neurology. 1992; 57:651-688.

43. Talairach J, Szikla G. Application of stereotactic concepts to the surgery of epilepsy. Acta neurochirurgica. Supplementum. 1980; 30:35-54.

44. Talairach J, Szikla G. [Amygdalo-hippocampal partial destruction by yttrium-90 in the treatment of certain epilepsies of rhinencephalic manifestation]. Neuro-Chirurgie. 1965; 11(3):233-240.

45. Bancaud J T J. La Stereo-ElectroEncephaloGraphie dans l'épilepsie. In: Cie M, ed. Paris1965.

46. Bancaud J, Talairach J, Waltregny P, Bresson M, Morel P. Activation by Megimide in the topographic diagnosis of focal cortical epilepsies (clinical EEG and SEEG study). Electroencephalography and clinical neurophysiology. 1969; 26(6):640.

47. Bancaud J, Talairach J, Waltregny P, Bresson M, Morel P. [Stimulation of focal cortical epilepsies by megimide in topographic diagnosis. (Clinical EEG and SEEG study)]. Revue neurologique. 1968; 119(3):320-325.

48. Bancaud J, Talairach J, Morel P, et al. "Generalized" epileptic seizures elicited by electrical stimulation of the frontal lobe in man. Electroencephalography and clinical neurophysiology. 1974; 37(3):275-282.

49. Bancaud J, Talairach J, Morel P, Bresson M. [Ammon's horn and amygdaline nucleus: clinical and electric effects of their stimulation in man]. Revue neurologique. 1966; 115(3):329-352.

50. Bancaud J, Talairach J, Lamarche M, Bonis A, Trottier S. [Neurophysiopathological hypothesis on startle epilepsy in man]. Revue neurologique. 1975; 131(8):559-571.

51. Bancaud J, Talairach J, Geier S, Bonis A, Trottier S, Manrique M. [Behavioral manifestations induced by electric stimulation of the anterior cingulate gyms in man]. Revue neurologique. 1976; 132(10): 705-724.

52. Munari C, Giallonardo A T, Brunet P, Broglin D, Bancaud J. Stereotactic investigations in frontal lobe epilepsies. Acta neurochirurgica. Supplementum. 1989; 46:9-12.

53. Munari C, Bossi L, Stoffels C, et al. [Cerebral concentrations of anticonvulsants in patients with epilepsy of tumoral origin (author's transl)]. Revue d'electroencephalographie et de neurophysiologie clinique. 1982; 12(1):38-43.

54. Munari C, Bancaud J, Bonis A, Buser P, Talairach J, Szikla G. [Role of the amygdala in the occurence of oro-alimentary signs of during epileptic seizures in man (author's transl)]. Revue d'electroencephalographie et de neurophysiologie clinique. 1979; 9(3):236-240.

55. Cardinale F, Lo Russo G. Stereo-electroencephalography safety and effectiveness: Some more reasons in favor of epilepsy surgery. Epilepsia. 2013; 54(8):1505-1506.

56. Sritharan D., Sarma S V (2014) Fragility in Dynamic Networks: Application to Neural Networks in the Epileptic Cortex. Neural Comput. 2014 October; 26(10):2294-327. doi: 10.1162/NECO_a_00644. Epub 2014 Jul. 24. PMID: 25058705

57. Gonzalez-Martinez J, Jirsa, V., Chauvel, P.; Sarma, S; Gale J; Najm, I. Modulating Epileptic Networks by SEEG guided laser ablations. American Epilepsy Society; 2015; Philadelpia.

63. Medvid R, Ruiz A, Komotar R J, et al. Current Applications of MRI-Guided Laser Interstitial Thermal Therapy in the Treatment of Brain Neoplasms and Epilepsy: A Radiologic and Neurosurgical Overview. AJNR. American journal of neuroradiology. 2015.

64. Lewis E C, Weil A G, Duchowny M, Bhatia S, Ragheb J, Miller I. M R-guided laser interstitial thermal therapy for pediatric drug-resistant lesional epilepsy. Epilepsia. 2015.

65. Hawasli A H, Bandt S K, Hogan R E, Werner N, Leuthardt E C. Laser ablation as treatment strategy for medically refractory dominant insular epilepsy: therapeutic and functional considerations. Stereotactic and functional neurosurgery. 2014; 92(6):397-404.
66. Gross R E, Mahmoudi B, Riley J P. Less is more: novel less-invasive surgical techniques for mesial temporal lobe epilepsy that minimize cognitive impairment. Current opinion in neurology. 2015; 28(2):182-191.
67. Gonzalez-Martinez J, Vadera S, Mullin J, et al. Robot-assisted stereotactic laser ablation in medically intractable epilepsy: operative technique. Neurosurgery. 2014; 10 Suppl 2:167-172; discussion 172-163.
68. Willie J T, Laxpati N G, Drane D L, et al. Real-time magnetic resonance-guided stereotactic laser amygdalohippocampotomy for mesial temporal lobe epilepsy. Neurosurgery. 2014; 74(6):569-584; discussion 584-565.
69. Willie J T, Gross R E. 202 Role of Repeat Ablation to Treat Seizure Recurrence Following Stereotactic Laser Amygdalohippocampotomy. Neurosurgery. 2015; 62 Suppl 1:233-234.
70. Waseem H, Osborn K E, Schoenberg M R, et al. Laser ablation therapy: An alternative treatment for medically resistant mesial temporal lobe epilepsy after age 50. Epilepsy & behavior: E&B. 2015; 51:152-157.
71. Tovar-Spinoza Z, Carter D, Ferrone D, Eksioglu Y, Huckins S. The use of MRI-guided laser-induced thermal ablation for epilepsy. Child's nervous system: ChNS: official journal of the International Society for Pediatric Neurosurgery. 2013; 29(11):2089-2094.
72. Sun X R, Patel N V, Danish S F. Tissue Ablation Dynamics During Magnetic Resonance-Guided, Laser-Induced Thermal Therapy. Neurosurgery. 2015; 77(1):51-58; discussion 58.
73. Esquenazi Y, Kalamangalam G P, Slater J D, et al. Stereotactic laser ablation of epileptogenic periventricular nodular heterotopia. Epilepsy research. 2014; 108(3):547-554.
74. Curry D J, Gowda A, McNichols R J, Wilfong A A. M R-guided stereotactic laser ablation of epileptogenic foci in children. Epilepsy & behavior: E&B. 2012; 24(4):408-414.
75. Engel J, Jr., Henry T R, Risinger M W, et al. Presurgical evaluation for partial epilepsy: relative contributions of chronic depth-electrode recordings versus FDG-PET and scalp-sphenoidal ictal EEG. Neurology. 1990; 40(11): 1670-1677.
76. Gonzalez-Martinez J. Convergence of Stereotactic Surgery and Epilepsy: The Stereoelectroencephalography Method. Neurosurgery. 2015; 62 Suppl 1:117-122.
77. Mullin J P, Shriver M, Alomar S A, Najm I, Gonzalez-Martinez J A. Is Stereotacticelectroencephalography Safe? A Systematic Review and Meta-Analysis of Stereoelectroencephalography-Related Complications. Neurosurgery. 2016 August; 63
78. Marquardt. An Algorithm for Least-Squares Estimation of Nonlinear Parameters. (1963) *Journal of the Society for Industrial and Applied Mathematics,* 11(2), 431-441.
79. Berg, A T. Identification of Pharmacoresistant Epilepsy. Neurol Clin 27 (2009) 1003-1013.
80. Sun F, Morrell M, Wharen R. Responsive Cortical Stimulation for the Treatment of Epilepsy. Neurotherapeutics. 2008 January; 5:68-74.
81. McIntosh A M, Kalnins R M, Mitchell L A, Fabinyi G C, Briellmann R S, Berkovic S F. Temporal lobectomy: long-term seizure outcome, late recurrence and risks for seizure recurrence. Brain. 2004 September; 127(Pt 9):2018-30. Epub 2004 Jun. 23.
82. Jeha L E, Najm I M, Bingaman W E, Khandwala F, Widdess-Walsh P, Morris H H, Dinner D S, Nair D, Foldvary-Schaeffer N, Prayson R A, Comair Y, O'Brien R, Bulacio J, Gupta A, Liiders H O. Predictors of outcome after temporal lobectomy for the treatment of intractable epilepsy. Neurology. 2006 Jun. 27; 66(12):1938-40.
83. See S J, Jehi L E, Vadera S, Bulacio J, Najm I, Bingaman W. Surgical Outcomes in Patients With Extratemporal Epilepsy and Subtle or Normal Magnetic Resonance Imaging Findings. Neurosurgery. 2013 July; 73(1): 68-7; discussion 76-7.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method of identifying an epileptogenic zone of a subject's brain, comprising:
   with a processor:
   receiving a plurality N of physiological brain signals that extend over a duration, the plurality N of physiological brain signals acquired from a plurality N of electrodes in said subject's brain;
   calculating within a time window a state transition matrix based on at least a portion of each of said plurality N of physiological brain signals, wherein the state transition matrix is a linear time invariant model of a network of N nodes corresponding to the plurality N of physiological brain signals;
   calculating, for each of the plurality N of physiological brain signals, a minimum norm of a perturbation on the state transition matrix that causes the network to transition from a stable state to an unstable state; and
   assigning a fragility metric to each of said plurality N of physiological brain signals based on the minimum norm of the perturbation for that physiological brain signal; and
   based on the fragility metric assigned to each of said plurality N of physiological brain signals, displaying, on a display device, an indication of a relative probability of each of said plurality o N of physiological brain signals being in the epileptogenic zone.

2. The method of identifying an epileptogenic zone of a subject's brain according to claim 1, wherein said calculating said state transition matrix comprises calculating a matrix A such that $$x(t+1)=Ax(t)$$

where x(t) is a state vector that describes activity of the network at time t, wherein activity of the network corresponds to said plurality N of physiological brain signals, and A is the state transition matrix for the time window.

3. The method of identifying an epileptogenic zone of a subject's brain according to claim 1, wherein said calculating said minimum norm of the perturbation comprises calculating a minimum norm of the perturbation for each row or column of the state transition matrix.

4. The method of identifying an epileptogenic zone of a subject's brain according to claim 3, wherein said assigning a fragility metric to each of said plurality N of physiological brain signals is based on a corresponding minimum norm of the perturbation calculated for each of the plurality N of physiological brain signals.

5. The method of identifying an epileptogenic zone of a subject's brain according to claim 4, further comprising generating a heat map as the indication of the relative probability of each of said plurality N of physiological brain signals being in the epileptogenic zone.

6. The method of identifying an epileptogenic zone of a subject's brain according to claim 1, further comprising displaying an indication of said fragility metric assigned to each of said plurality N of physiological brain signals at a plurality of points in time within said duration.

7. The method of identifying an epileptogenic zone of a subject's brain according to claim 1, wherein each of said plurality N of physiological brain signals corresponds to one of the plurality N of electrodes in said subject's brain.

8. A non-transitory computer-readable medium for identifying an epileptogenic zone of a subject's brain comprising computer-executable code, said code when executed by a computer causes the computer to:
receive a plurality N of electrical signals that extend over a duration, the plurality N of physiological brain signals acquired from a plurality N of electrodes in said subject's brain;
calculate within a time window a state transition matrix based on at least a portion of each of said plurality N of physiological brain signals, wherein the state transition matrix is a linear time invariant model of a network of N nodes corresponding to the plurality N of physiological brain signals;
calculate, for each of the plurality N of physiological brain signals, a minimum norm of a perturbation on the state transition matrix that causes the network to transition from a stable state to an unstable state;
assign a fragility metric to each of said plurality N of physiological brain signals based on the minimum norm of the perturbation for that physiological brain signal; and
based on the fragility metric assigned to each of said plurality N of physiological brain signals, display, on a display device, an indication of a relative probability of each of said plurality o N of physiological brain signals being in the epileptogenic zone.

9. The non-transitory computer-readable medium according to claim 8, wherein said code when executed by a computer causes the computer to calculate said state transition matrix by calculating a matrix A such that $$x(t+1)=Ax(t)$$

where x(t) is a state vector that describes activity of the network at time t, and A is the state transition matrix for the time window.

10. The non-transitory computer-readable medium according to claim 8, wherein said code when executed by a computer causes the computer to calculate said minimum norm of the perturbation by calculating a minimum norm of the perturbation for each row or column of the state transition matrix.

11. The non-transitory computer-readable medium according to claim 10, wherein said code when executed by a computer causes the computer to assign a fragility metric to each of said plurality N of physiological brain signals by assigning a fragility metric based on a corresponding minimum norm of the perturbation calculated for each of the plurality N of physiological brain signals.

12. The non-transitory computer-readable medium according to claim 11, wherein said code when executed by a computer further causes the computer to generate a heat map as the indication of the relative probability of each of said plurality N of physiological brain signals being in the epileptogenic zone.

13. The non-transitory computer-readable medium according to claim 8, wherein said code when executed by a computer further causes the computer to display an indication of said fragility metric assigned to each of said plurality N of physiological brain signals at a plurality of points in time within said duration.

14. The non-transitory computer-readable medium according to claim 8, wherein each of said plurality N of physiological brain signals corresponds to one of the plurality N of electrodes in said subject's brain.

15. A system for identifying an epileptogenic zone of a subject's brain comprising a computer configured to:
receive a plurality N of physiological brain signals that extend over a duration, the plurality N of physiological brain signals acquired from a plurality N of electrodes in said subject's brain;
calculate within a time window a state transition matrix based on at least a portion of each of said plurality N of physiological brain signals, wherein the state transition matrix is a linear time invariant model of a network of N nodes corresponding to the plurality N of physiological brain signals;
calculate, for each of the plurality N of physiological brain signals, a minimum norm of a perturbation on the state transition matrix that causes the network to transition from a stable state to an unstable state;
assign a fragility metric to each of said plurality N of physiological brain signals based on the minimum norm of the perturbation for that physiological brain signal; and
based on the fragility metric assigned to each of said plurality N of physiological brain signals, display, on a display device, an indication of a relative probability of each of said plurality o N of physiological brain signals being in the epileptogenic zone.

16. The system for identifying an epileptogenic zone of a subject's brain according to claim 15, wherein said computer is further configured to calculate said state transition matrix by calculating a matrix A such that $$x(t+1)=Ax(t)$$

where x(t) is a state vector that describes activity of the network at time t, and A is the state transition matrix for the time window.

17. The system for identifying an epileptogenic zone of a subject's brain according to claim 15, wherein said computer is further configured to calculate said minimum norm of the perturbation by calculating a minimum norm of the perturbation for each row or column of the state transition matrix.

18. The system for identifying an epileptogenic zone of a subject's brain according to claim 17, wherein said computer is further configured to assign a fragility metric to each of said plurality N of physiological brain signals by assigning a fragility metric based on a corresponding minimum norm of the perturbation calculated for each of the plurality N of physiological brain signals.

19. The system for identifying an epileptogenic zone of a subject's brain according to claim 18, wherein said computer is further configured to generate a heat map as the indication of the relative probability of each of said plurality N of physiological brain signals being in the epileptogenic zone.

20. The system for identifying an epileptogenic zone of a subject's brain according to claim 19, wherein said computer is further configured to display an indication of said fragility metric assigned to each of said plurality N of physiological brain signals at a plurality of points in time within said duration.

21. The system for identifying an epileptogenic zone of a subject's brain according to claim 15, wherein each of said plurality N of physiological brain signals corresponds to one of the plurality N of electrodes in said subject's brain.

\* \* \* \* \*